(12) United States Patent
Balijepalli et al.

(10) Patent No.: US 12,195,787 B2
(45) Date of Patent: Jan. 14, 2025

(54) DNA NANOTECHNOLOGY-BASED BIOMARKER MEASUREMENT PLATFORM

(71) Applicant: Government of the United States of America, as represented by the Secretary of Commerce, Gaithersburg, MD (US)

(72) Inventors: Arvind Kumar Balijepalli, Washington, DC (US); Jacob Michael Majikes, Gaithersburg, MD (US)

(73) Assignee: GOVERNMENT OF THE UNITED STATES OF AMERICA, AS REPRESENTED BY THE SECRETARY OF COMMERCE, Gaithersburg, MD (US)

( * ) Notice: Subject to any disclaimer, the term of this patent is extended or adjusted under 35 U.S.C. 154(b) by 760 days.

(21) Appl. No.: 17/360,008

(22) Filed: Jun. 28, 2021

(65) Prior Publication Data

US 2021/0403988 A1 Dec. 30, 2021

Related U.S. Application Data

(60) Provisional application No. 63/045,366, filed on Jun. 29, 2020.

(51) Int. Cl.
*C12Q 1/6823* (2018.01)
*G01N 33/53* (2006.01)

(52) U.S. Cl.
CPC ....... *C12Q 1/6823* (2013.01); *G01N 33/5308* (2013.01)

(58) Field of Classification Search
CPC .............. C12Q 1/6823; C12Q 1/6816; C12Q 2563/137; C12Q 2565/519; C12Q 2565/067; G01N 33/5308
See application file for complete search history.

(56) References Cited

U.S. PATENT DOCUMENTS

| | | | |
|---|---|---|---|
| 10,550,145 B2* | 2/2020 | Han | C12N 15/10 |
| 2002/0137058 A1* | 9/2002 | Mirkin | C12Q 1/6837 |
| | | | 536/23.1 |

(Continued)

OTHER PUBLICATIONS

Zhou, Lifeng et al. "Paper Origami-Inspired Design and Actuation of DNA Nanomachines with Complex Motions." Small (Weinheim an der Bergstrasse, Germany) vol. 14,47 (2018) (Year: 2018).*

(Continued)

*Primary Examiner* — P. Kathryn Wright
*Assistant Examiner* — Curtis A Thompson
(74) *Attorney, Agent, or Firm* — Office of Chief Counsel for National Institute of Standards and Technology

(57) ABSTRACT

A biomarker signal amplifier amplifies chemical analyte binding and includes: a surface strand disposed on an analysis substrate and including an exchange region; a particle strand hybridized to the surface strand in an absence of a chemical analyte that preferentially hybridizes to the exchange region as compared with the particle strand, and the particle strand is dissociated from the surface strand when the surface strand is in a presence of the chemical analyte; and a reporter particle attached to the particle strand and disposed proximate to the analysis substrate when the particle strand is hybridized to the surface strand in absence of the chemical analyte and that changes the electrical potential of the analysis substrate depending on whether the particle strand is hybridized to the surface strand.

27 Claims, 12 Drawing Sheets

(56) References Cited

U.S. PATENT DOCUMENTS

| | | | | |
|---|---|---|---|---|
| 2013/0071839 | A1* | 3/2013 | Seelig | C12Q 1/6876 |
| | | | | 977/902 |
| 2017/0073682 | A1* | 3/2017 | Zhang | C12N 15/115 |
| 2019/0137443 | A1 | 5/2019 | Balijepalli et al. | |
| 2020/0264129 | A1 | 8/2020 | Balijepalli et al. | |
| 2021/0088463 | A1 | 3/2021 | Balijepalli et al. | |
| 2021/0348218 | A1* | 11/2021 | Sardar | G01N 21/658 |
| 2022/0325332 | A1* | 10/2022 | Balijepalli | C12Q 1/6825 |
| 2023/0227520 | A1* | 7/2023 | Elgamacy | A61P 7/00 |
| | | | | 514/7.9 |

OTHER PUBLICATIONS

Fan et al., Recent Advances in Dynamic DNA Nanodevice, 2023, Chemistry, 5, 1781-1803 (Year: 2023).*

Kuzyk, et al. Reconfigurable 3D plasmonic metamolecules, Jul. 6, 2014, Nature Materials, 13, 862-866. (Year: 2014).*

Kroener et al., Electrical Actuation of a DNA Origami Nanolever on an Electrode, 2017, Journal of the American Chemical Society, 139, 16510-16513 (Year: 2017).*

Li et al., Design of DNA nanostructure-based interfacial probes for the electrochemical detection of nucleic acids directly in whole blood, Nov. 2017, Chemical Science, 9, 979-984 (Year: 2017).*

Zhan et al., Reconfigurable Three-Dimensional Gold Nanorod Plasmonic Nanostructures Organized on DNA Origami Tripod, 2017, ACS Nano, 11, 1172-1179 (Year: 2017).*

Zhou, et al. Paper Origami-Inspired Design and Actuation of DNA Nanomachines with Complex Motions, 2018, Small, 14, 1802580 (1-12) (Year: 2018).*

Sakai et al. DNA Aptamers for the Functionalisation of DNA Origami Nanostructures, Nov. 2018, Genes, 9, 571, 1-20 (Year: 2018).*

Douglas et al. A Logic-Gated Nanorobot for Targeted Transport of Molecular Payloads, 2012, Science, 335, 831-834 (Year: 2012).*

Yan, J., et al., "Novel Rolling Circle Amplification and DNA Origami-Based DNA Belt-Involved Signal Amplification Assay for Highly Sensitive Detection of Prostate-SpecificAntigen (PSA)", ACS Applied Materials and Interfaces, 2014, p. 2372-20377, vol. 6.

Phao, W.-W et al., "Exciton-Plasmon Interactions between CdS Quantum Dots and AgNanoparticles in Photoelectrochemical System and Its Biosensing Application", Analytical Chemistry, 2012, p. 5892-5897, vol. 84.

Golub, E., et al., "Electrochemical,Photoelectrochemical, and Surface Plasmon Resonance Detection of Cocaine UsingSupramolecular Aptamer Complexes and Metallic or Semiconductor Nanoparticles", Anal.Chem., 2009, p. 9291-9298, vol. 81.

Sakata, T., et al., "Detection sensitivity of genetic field effect transistor combinedwith charged nanoparticle-DNA conjugate", International Conference on Microtechnologies in Medicine and Biology, 2006, p. 97-100, doi: 10.1109/MMB.2006.251500.

Wang, X. et al., "Tetrahedral DNA Nanostructure-decorated Electrochemical Platform forSimple and Ultrasensitive EGFR Genotyping of Plasma ctDNA", Analyst, 2020, p. 4671-4679, vol. 145 , doi:10.1039/D0AN00591F.

Le, S. T. et al., "Rapid, quantitative therapeutic screening for Alzheimer's enzymes enabledby optimal signal transduction with transistors", Analyst, 2020, p. 2925-2936, vol. 145.

Liu, Y., et al., "Tuning Biosensor Cross-Reactivity Using Aptamer Mixtures", Analytical Chemistry, 2020, p. 5041-5047, vol. 92, doi: 10.1021/acs.analchem.9b05339.

Wu, D. et al., "Dual-Aptamer Modified Graphene Field-Effect Transistor Nanosensor forLabel-Free and Specific Detection of Hepatocellular Carcinoma-Derived Microvesicles", Anal. Chem., 2020, p. 4006-4015, vol. 92, doi:10.1021/acs.analchem.9b05531.

Le, S. T. et al., "Quantum capacitance-limited MoS2 biosensors enable remote label-freeenzyme measurements", Nanoscale, 2019, p. 15622-15632, vol. 11.

Zhang, D. Y., et al., "Control of DNA Strand Displacement Kinetics Using Toehold Exchange", J. Am. Chem. Soc., 2009, p. 17303-17314, vol. 131.

Zhang, D. Y., et al., "Dynamic DNA nanotechnology using stranddisplacement reactions", Nature Chemistry, 2011, p. 103-113, vol. 3.

Zhang, Z. et al., "A DNA-Origami chip platform for label-free SNP genotyping using toehold-mediated strand displacement", Small, 2010, p. 1854-1858, vol. 6 No. 17.

Hiwang, M. T. et al., "Highly specific SNP detection using 2D graphene electronics andDNA strand displacement", PNAS, 2016, p. 7088-7093, vol. 113 No. 26.

Chan, M. S. et al., "Reversible reconfiguration of high-order DNA nanostructures byemploying G-quartet toeholds as adhesive units", Nanoscale, 2020, p. 2464-2471, vol. 12.

Hu, P. et al., "Cooperative Toehold: A Mechanism To Activate DNA Strand Displacementand Construct Biosensors", Analytical Chemistry, 2018, p. 9751-9760, vol. 90.

Chandrasekaran, A. R. et al., "DNA nanotechnology approaches for microRNA detection and diagnosis", Nucleic Acids Research, 2019, p. 10489-10505, vol. 47 No. 20.

Puchkova, A. et al., "DNA Origami Nanoantennas with over 5000-fold FluorescenceEnhancement and Single-Molecule Detection at 25 μM", Nano Letters, 2015, p. 8354-8359, vol. 15.

Daems, D. et al., "Three-Dimensional DNA Origami as Programmable Anchoring Points for Bioreceptors in Fiber Optic Surface Plasmon Resonance Biosensing", ACS Applied Materials and Interfaces, 2018, p. 23539-23547, vol. 10.

\* cited by examiner (A)

(B)

DNA NANOTECHNOLOGY-BASED BIOMARKER MEASUREMENT PLATFORM

CROSS REFERENCE TO RELATED APPLICATIONS

The application claims priority to U.S. Provisional Patent Application Ser. No. 63/045,366 filed Jun. 29, 2020, the disclosure of which is incorporated herein by reference in its entirety.

STATEMENT REGARDING FEDERALLY SPONSORED RESEARCH

This invention was made with United States Government support from the National Institute of Standards and Technology (NIST), an agency of the United States Department of Commerce. The Government has certain rights in the invention.

BRIEF DESCRIPTION

Disclosed is a biomarker signal amplifier for amplifying analyte binding, the biomarker signal amplifier comprising: an analysis substrate; a surface strand disposed on the analysis substrate and comprising an exchange region; a particle strand hybridized to the surface strand in an absence of a chemical analyte that preferentially hybridizes to the exchange region as compared with the particle strand, and the particle strand is dissociated from the surface strand when the surface strand is in a presence of the chemical analyte; and a reporter particle attached to the particle strand and disposed proximate to the analysis substrate when the particle strand is hybridized to the surface strand in absence of the chemical analyte and that changes the electrical potential of the analysis substrate depending on whether the particle strand is hybridized to the surface strand.

Disclosed is a DNA switch for amplifying analyte binding, the DNA switch comprising: an analysis substrate; a DNA nanostructure framework disposed on the analysis substrate comprising a nucleic acid core, a first helix strand protruding from the nucleic acid core and attached to the analysis substrate, and a second helix strand protruding from the nucleic acid core such that the second helix strand is hybridized to the first helix strand in an absence of a chemical analyte that preferentially hybridizes to the first helix strand as compared with the second helix strand, and the second helix strand dissociates from the first helix strand when the first helix strand is in a presence of the chemical analyte; a particle strand hybridized to the second helix strand; and a reporter particle attached to the particle strand and disposed proximate to the analysis substrate when the second helix strand is hybridized to the first helix strand in absence of the chemical analyte and that changes the electrical potential of the analysis substrate depending on whether the second helix strand is hybridized to the first helix strand.

Disclosed is a sensor array for performing spatially resolved biomarker measurements, the sensor array comprising a plurality of the DNA switches arranged in an array, wherein the plurality of first helix strands independently hybridize separate chemical analytes and produce individual electrical signals indicative of presence and absence of the chemical analyte at individual first helix strands.

BRIEF DESCRIPTION OF THE DRAWINGS

The following description cannot be considered limiting in any way. With reference to the accompanying drawings, like elements are numbered alike.

DETAILED DESCRIPTION

Figure 1:
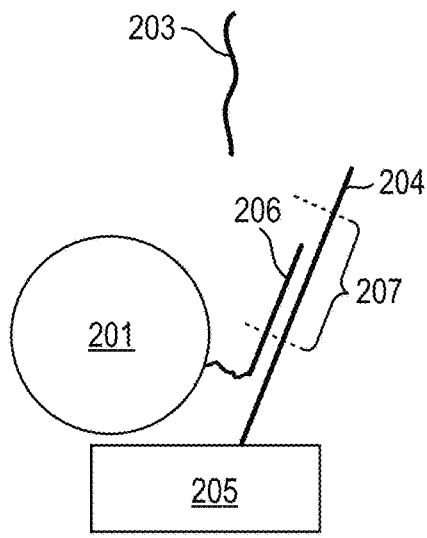
FIG. 1 shows a biomarker signal amplifier before binding a chemical analyte in panel A, during binding of the chemical analyte in panel B, and after binding the chemical analyte in panel C, wherein the biomarker signal amplifier uses engineered DNA strand-displacement combined with a reporter particle.
Figure 1:
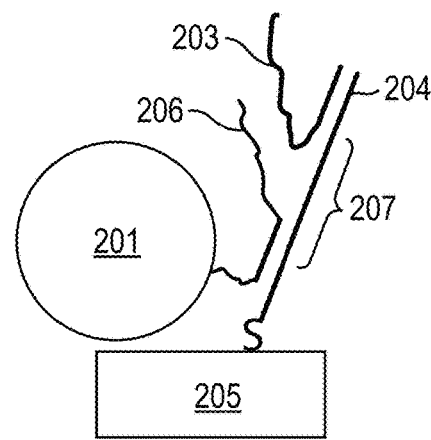
Figure 1:
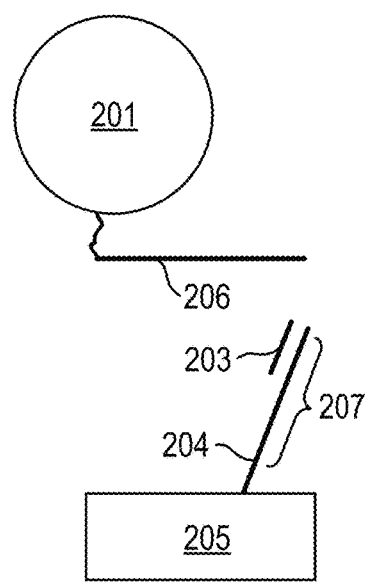

A detailed description of one or more embodiments is presented herein by way of exemplification and not limitation.

Aptamers, and in particular single-stranded (SS) oligonucleotides or peptides, are molecules used as diagnostic reagents and potential antibody replacements for the development of biomolecular nanosensors, due to their high affinity, specificity, and stability for analytes of interest.

Numerous aptamer-based sensors (aptasensors or aptamer beacons) have been developed to monitor the interaction with targets by measuring electron transfer, color change, or fluorescence quenching occurring following the aptamer binding to the target.

In view of the features of current aptamer-based sensors, achievement of specificity, sensitivity, and stability of the aptamer-based sensors with current approach can often be challenging. There is a need for broader-based DNA-based sensor technology for a wider class of chemical analytes.

It has been discovered that a DNA nanotechnology-based biomarker measurement platform uses precise addressability of DNA nanotechnology constructs to quantitatively sense biomolecules with high sensitivity, specificity, and reproducibility. Engineering DNA nanostructures integrated in the DNA nanotechnology-based biomarker measurement platform provides tunable gain elements, in situ calibration of chemical concentration, and robust statistical sampling for biochemical measurement that exceed conventional technology. The DNA nanotechnology-based biomarker measurement platform is compatible with signal readout strategies that include, e.g., electronic or optical readouts, and can be chip scale. The DNA nanotechnology-based biomarker measurement platform is applicable in clinical diagnostics, therapeutic development, bionanotechnology and other applications.

The DNA nanotechnology-based biomarker measurement platform includes sensitive electronic readout for label-free measurements of DNA and multi-analyte and multi-site measurements on chip. Further, the DNA nanotechnology-based biomarker measurement platform provides precise colocalization of analyte-binding/signal-amplification motifs for characterization as well as the capability to tune, for individual motifs, binding affinity. This capability reduces error rates of the measurements and provides more robust results as compared with conventional technology. The DNA nanotechnology-based biomarker measurement platform solves the long-standing problem of measurement specificity that has plagued applications in clinical diagnostics and other areas of healthcare. The nanoscale features of the DNA nanotechnology-based biomarker measurement platform provides multiplexed measurements and rigorous sampling on-chip to improve accuracy over conventional devices.

Various molecular structures described herein involve nucleic acids. As used herein, a "nucleic acid" can include deoxyribonucleic acid (DNA), ribonucleic acid (RNA), or artificial nucleic acids, such as a peptide nucleic acid (PNA). The molecular structure may include one type of nucleic acid (e.g., DNA), or more than one type in some cases, which may form part of the same molecule or different molecules assembled together in a supramolecular assembly defining the overall molecular structure. Typically, the nucleic acid is a polymeric molecule including one or more "bases" (usually nitrogenous) connected to a backbone structure, which can be a sugar-phosphate backbone (e.g., as in DNA or RNA) or a peptide backbone (e.g., as in PNA).

The sugars within the nucleic acid, when present, may be, for example, ribose sugars (as in RNA), or deoxyribose sugars (as in DNA). In some cases, the nucleic acid can include ribose and deoxyribose sugars. Examples of bases that may be found within a nucleic acid include, but are not limited to, the naturally-occurring bases (e.g., adenosine or "A," thymidine or "T," guanosine or "G," cytidine or "C," or uridine or "U"). The bases typically interact on a specific basis (i.e., guanosine interacts with cytidine via hydrogen bonding and vice versa, and adenosine interacts with thymidine or uridine via hydrogen bonding and vice versa). In some cases, the nucleic acid may include nucleoside analogs (e.g., 2-aminoadenosine, 2-thiothymidine, inosine, pyrrolo-pyrimidine, 3-methyladenosine, C5-bromouridine, C5-fluorouridine, C5-iodouridine, C5-propynyluridine, C5-propynylcytidine, C5-methylcytidine, 7-deazaadenosine, 7-deazaguanosine, 8-oxoadenosine, 8-oxoguanosine, 06-methylguanosine, 2-thiocytidine, 2-aminopurine, 2-amino-6-chloropurine, 2,6-diaminopurine, hypoxanthine), chemically or biologically modified bases (e.g., methylated bases), intercalated bases, modified sugars (2'-fluororibose, arabinose, or hexose), modified phosphate moieties (e.g., phosphorothioates or 5'-N-phosphoramidite linkages), or other naturally and non-naturally occurring bases substitutable into the nucleic acid, including substituted and unsubstituted aromatic moieties. Other suitable base or backbone modifications can occur.

The nucleic acid can be single-stranded or double-stranded, i.e., formed of two strands (or of the same strand looped back on itself, such as in a hairpin turn or a stem-loop structure) associated with each other via hydrogen bonding, e.g., via guanosine/cytidine base-pair interactions, adenosine/thymidine base-pair interactions, adenosine/uridine base-pair interactions, etc.

The nucleic acids can be present within a molecular structure as a bundle, which can include two or more non-complementary nucleic acid portions associated with each other. The nucleic acids forming the bundles can be single stranded or double stranded, and the non-complementary nucleic acid portions can be part of the same nucleic acid molecule or part of different nucleic acid molecules. For instance, there may be 2, 3, 4, 5, 6, 8, 10, 12, 14, 16, 18, 20, 24, 30, 42, 54, 66, 78, 90, or more non-complementary nucleic acid portions associated with each other as part of a bundle. There can be other nucleic acid strands associated with one or more portions of the nucleic acids forming the nucleic acid bundle, e.g., to provide stability.

It should be noted that, in a bundle of nucleic acid, not all of the nucleic acid strands need run from one end of the bundle to the other. For example, one or more nucleic acid strands may run from a first end of the bundle, through a hairpin turn or a stem-loop structure, back to the first end of the bundle (or may go through more than one hairpin turn or a stem-loop structure, in some cases); or a nucleic acid strand may end within the bundle.

In some cases, the bundles can define a nanotube. The nanotube can have a hollow center, with nucleic acid strands arranged around the center (thus, a double strand of DNA, by itself, is not a nanotube, as the two sugar-phosphate backbones forming the DNA are interconnected by bases hydrogen bonded to each other, which thus does not result in a hollow center). The nanotube may be circular or elliptical, or in some cases, the nanotube may have polygonal shapes such as a hexagon. In some cases, the nanotube may have more than one hollow center, e.g., having the shape of a lemniscate. Non-limiting examples of such nanotubes are shown in FIG. 3A (perspective view of a six-helix nucleic acid bundle), FIG. 3B (side view of the six-helix nucleic acid bundle shown in panel A), FIG. 3C (cross-section along line A-A of the six-helix nucleic acid bundle shown in panel B), FIG. 3D (a ten-helix nucleic acid bundle, having a lemniscate shape with two hollow centers; thus, more than one hollow center may be present within the nanotube), and FIG. 3E (bundles with the number of nucleic acid strands present within the nanotube shown in the center of each nanotube). The nucleic acid portions forming the bundled nanotube may be part of the same nucleic acid molecule or may be part of different nucleic acid molecules. In some cases, the nanotube may be formed from an even number of nucleic acid strands (e.g., 4, 6, 8, 10, 12, etc.). In certain embodiments, other molecules may be present within the nanotube, for example, to provide stability to the nanotube structure.

In some embodiments, one or more of the nucleic acid bundles or nanotubes within the molecular structure may be fabricated from one or more relatively long nucleic acids, e.g., having lengths of at least about 500 nucleotides, at least about 1,000 nucleotides, at least about 3,000 nucleotides, at least about 10,000 nucleotides, at least about 30,000 nucleotides, etc. Such a nucleic acid may be referred to as a nucleic acid scaffold. The nucleic acid scaffold may form a single bundle or nanotube, or may include different parts of different bundles or nanotubes in the final molecular structure. For instance, a nucleic acid scaffold may wrap in various ways around the molecular structure, e.g., forming various nucleic acid bundles or nanotubes defining the molecular structure. In some cases, a nucleic acid may form a first portion of a nucleic acid bundle and a second portion of the same nucleic acid bundle (or a different one), where the first and second portions forming the nucleic acid bundle are not complementary. In one set of embodiments, the nucleic acid scaffolds are substantially free of self-complementary regions and/or repeat units, as discussed below. In certain embodiments of the invention, the nucleic acid scaffolds are immobilized to form one or more bundles or nanotubes, and ultimately a three-dimensional structure, using one or more nucleic acid stabilizers able to associate with two or more portions of the nucleic acid. In certain embodiments, the structures can have other shapes, e.g., notched rectangles, as well as other planar or three-dimensional structures.

One source of a nucleic acid having such characteristics is bacteriophage DNA, for example, M13 bacteriophage. The DNA in such bacteriophages may be single stranded DNA, and have substantially few self-complementary regions (e.g., only 2 hairpin regions may form), and a length of about 7,000 nucleotides. The DNA can be removed from the bacteriophage using DNA isolation techniques known to those of ordinary skill in the art, for example, by using lysis buffer (e.g., comprising an alkaline environment or surfactant) followed by centrifugation at greater than 10,000 RCF (relative centrifugal force) to separate the DNA.

The molecular structure may be stabilized, in some cases, by nucleic acid stabilizers able to associate with two or more nucleic acid portions. For example, a nucleic acid stabilizer may include a first portion complementary to a first nucleic acid strand (e.g., a nucleic acid scaffold) and a second portion complementary to a second nucleic acid strand. The first and second portions may be part of the same nucleic acid molecule, or may be part of different molecules. In some cases, the nucleic acid stabilizer may be formed essentially from nucleic acid. A nucleic acid stabilizer may have a length of between about 20 nucleotides and about 100 nucleotides, for example, between about 35 nucleotides and about 45 nucleotides, or about 40 nucleotides. As the first portion of the nucleic acid stabilizer binds to the first nucleic acid portion and the second portion binds to the second nucleic acid portions, the two portions are substantially immobilized, relative to each other, due to the presence of the nucleic acid stabilizer. Thus, the two portions are not able to move apart, or at least are not able to move far apart, and remain associated together. By using a plurality of nucleic acid stabilizers, e.g., targeted to different nucleic acids or different portions of nucleic acids, one or more nucleic acids can be stabilized in a substantially rigid configuration, e.g., as a bundle or a nanotube. In addition, these can further be configured as part of larger molecular structures. A technique for forming nucleic acid stabilizers is found in Rothemund, P. W. K., "Folding DNA to Create Nanoscale Shapes and Patterns," Nature, 440:297-302 (2006).

As used herein, "microRNA" or "miRNA" describes small, non-coding RNA molecules, generally about 15 to about 50 nucleotides in length, specifically 17-23 nucleotides, that can play a role in regulating gene expression through, e.g., a process referred to as RNA interference (RNAi). RNAi describes a phenomenon whereby the presence of an RNA sequence that is complementary or anti-sense to a sequence in a target gene messenger RNA (mRNA) results in inhibition of expression of the target gene. Here, miRNAs are processed from hairpin precursors of about 70 or more nucleotides (pre-miRNA) that are derived from primary transcripts (pri-miRNA) through sequential cleavage by RNAse III enzymes. Moreover, miR-Base is a comprehensive microRNA database located at www.mirbase.org, incorporated by reference herein in its entirety for all purposes.

The RNAi can be transcribed as an RNA precursor having a hairpin-like structure, cleaved by a dsRNA-cleaving enzyme having RNase III cleavage activity, and integrated into a protein complex called RISC and can be involved in the suppression of translation of mRNA. The term "miRNA" includes not only a "miRNA" represented by a particular nucleotide sequence but a "miRNA" including a precursor of the "miRNA" (pre-miRNA or pri-miRNA) and having biological functions equivalent to miRNAs encoded by these, e.g., a "miRNA" encoding a congener (i.e., a homolog or an ortholog), a variant such as a genetic polymorph, and a derivative. Such a "miRNA" encoding a precursor, a congener, a variant, or a derivative can be specifically identified using miRBase Release 22 (http://www.mirbase.org/), and examples thereof can include a "miRNA" having a nucleotide sequence hybridizing to a complementary nucleotide sequence. It is contemplated that miRNA can be a gene product of a miR gene. Such a gene product includes a mature miRNA (e.g., a 15- to 25-nucleotide or 19- to 25-nucleotide non-coding RNA involved in the suppression of translation of mRNA as described above) or a miRNA precursor (e.g., pre-miRNA or pri-miRNA as described above).

Complementary polynucleotide and similar referents such as complementary strand or reverse strand includes a polynucleotide in a complementary relationship based on A:T (U) and G:C base pairs with the full-length sequence of a polynucleotide or a nucleotide sequence derived from the nucleotide sequence by the replacement of U with T, or a partial sequence thereof (here, this full-length or partial sequence is referred to as a plus strand for the sake of convenience). However, such a complementary strand is not limited to a sequence completely complementary to the nucleotide sequence of the target plus strand and may have a complementary relationship to an extent that permits hybridization under stringent conditions to the target plus strand.

The term "$T_m$ value" refers to a temperature at which the double-stranded moiety of a polynucleotide is denatured into single strands so that the double strands and the single strands exist at a ratio of 1:1.

The term "aptamer" indicates oligonucleic acid or peptide molecules that are capable to bind a specific target. It is contemplated that the aptamer can include single-stranded oligonucleotides and chemically synthesized peptides that have been engineered through repeated rounds of in vitro selection, or equivalent techniques identifiable by a skilled person, to bind to various targets.

As used herein, the term "nucleotide" refers to a molecule that includes a sugar and at least one phosphate group, and optionally also includes a nucleobase. A nucleotide that lacks a nucleobase can be referred to as "abasic." Nucleotides include deoxyribonucleotides, modified deoxyribonucleotides, ribonucleotides, modified ribonucleotides, peptide nucleotides, modified peptide nucleotides, modified phosphate sugar backbone nucleotides, and mixtures thereof. Examples of nucleotides include adenosine monophosphate (AMP), adenosine diphosphate (ADP), adenosine triphosphate (ATP), thymidine monophosphate (TMP), thymidine diphosphate (TDP), thymidine triphosphate (TTP), cytidine monophosphate (CMP), cytidine diphosphate (CDP), cytidine triphosphate (CTP), guanosine monophosphate (GMP), guanosine diphosphate (GDP), guanosine triphosphate (GTP), uridine monophosphate (UMP), uridine diphosphate (UDP), uridine triphosphate (UTP), deoxyadenosine monophosphate (dAMP), deoxyadenosine diphosphate (dADP), deoxyadenosine triphosphate (dATP), deoxythymidine monophosphate (dTMP), deoxythymidine diphosphate (dTDP), deoxythymidine triphosphate (dTTP), deoxycytidine diphosphate (dCDP), deoxycytidine triphosphate (dCTP), deoxyguanosine monophosphate (dGMP), deoxyguanosine diphosphate (dGDP), deoxyguanosine triphosphate (dGTP), deoxyuridine monophosphate (dUMP), deoxyuridine diphosphate (dUDP), and deoxyuridine triphosphate (dUTP).

The term "nucleotide" also include any "nucleotide analogue which is a type of nucleotide that includes a modified nucleobase, sugar or phosphate moiety compared to naturally occurring nucleotides. Exemplary modified nucleobases that can be included in a polynucleotide, whether having a native backbone or analogue structure, include, inosine, xathanine, hypoxathanine, isocytosine, isoguanine, 2-aminopurine, 5-methylcytosine, 5-hydroxymethyl cytosine, 2-aminoadenine, 6-methyl adenine, 6-methyl guanine, 2-propyl guanine, 2-propyl adenine, 2-thiouracil, 2-thiothymine, 2-thiocytosine, 15-halouracil, 15-halocytosine, 5-propynyl uracil, 5-propynyl cytosine, 6-azo uracil, 6-azo cytosine, 6-azo thymine, 5-uracil, 4-thiouracil, 8-halo adenine or guanine, 8-amino adenine or guanine, 8-thiol adenine or guanine, 8-thioalkyl adenine or guanine, 8-hydroxyl adenine or guanine, 5-halo substituted uracil or cytosine, 7-methylguanine, 7-methyladenine, 8-azaguanine, 8-azaadenine, 7-deazaguanine, 7-deazaadenine, 3-deazaguanine, 3-deazaadenine or the like. As is known in the art, certain nucleotide analogues cannot become incorporated into a polynucleotide, for example, nucleotide analogues such as adenosine 5'-phosphosulfate.

As used herein, the term "polynucleotide" refers to a molecule that includes a sequence of nucleotides that are bonded to one another. Examples of polynucleotides include deoxyribonucleic acid (DNA), ribonucleic acid (RNA), and analogues thereof. A polynucleotide can be a single stranded sequence of nucleotides, such as RNA or single stranded DNA, a double stranded sequence of nucleotides, such as double stranded DNA, or can include a mixture of a single stranded and double stranded sequences of nucleotides. Double stranded DNA (dsDNA) includes genomic DNA, and PCR and amplification products. Single stranded DNA (ssDNA) can be converted to dsDNA and vice-versa. The precise sequence of nucleotides in a polynucleotide can be known or unknown. The following are exemplary examples of polynucleotides: a gene or gene fragment (for example, a probe, primer, expressed sequence tag (EST) or serial analysis of gene expression (SAGE) tag), genomic DNA, genomic DNA fragment, exon, intron, messenger RNA (mRNA), transfer RNA, ribosomal RNA, ribozyme, cDNA, recombinant polynucleotide, synthetic polynucleotide, branched polynucleotide, plasmid, vector, isolated DNA of any sequence, isolated RNA of any sequence, nucleic acid probe, primer or amplified copy of any of the foregoing.

As used herein, "hybridize" refers to noncovalently binding a first polynucleotide to a second polynucleotide. The strength of the binding between the first and second polynucleotides increases with the complementarity between those polynucleotides.

As used herein, the term "protein" refers to a molecule that includes a polypeptide that is folded into a three-dimensional structure. The polypeptide includes moieties that, when folded into the three-dimensional structure, impart the protein with biological activity.

The term "sensor" indicates a device that measures a physical quantity and converts it into a signal which can be read by an observer or by an instrument. The sensors can be calibrated against a known standard.

The term "detect" or "detection" indicates determination of the existence or presence of a chemical analyte or other target or signal in a limited portion of space, including but not limited to a sample, a reaction mixture, a molecular complex and a substrate including a platform and an array. Detection is "quantitative" when it refers, relates to, or involves the measurement of quantity or amount of chemical analyte or signal (also referred as quantification), which includes but is not limited to any analysis designed to determine the amounts or proportions of the chemical analyte or signal. Detection is "qualitative" when it refers, relates to, or involves identification of a quality or kind of the chemical analyte or signal in terms of relative abundance to another chemical analyte or signal, which is not quantified. An "optical detection" indicates detection performed through visually detectable signals: spectra or images from a chemical analyte or a probe attached to the chemical analyte. An "electrical detection" indicates detection performed through electrically detectable signals: voltage, electrical current, induction, or capacitance from a chemical analyte or a probe attached to the chemical analyte.

The term "chemical analyte" refers to a substance, compound, or component whose presence or absence in a sample is detected through hybridization. Chemical analytes include biomolecules and in particular biomarkers. The term "biomolecule" indicates a substance compound or component associated to a biological environment including but not limited to sugars, amino acids, peptides proteins, oligonucleotides, polynucleotides, polypeptides, organic molecules, haptens, epitopes, biological cells, parts of biological cells, vitamins, hormones, and the like. The term "biomarker" indicates a biomolecule that is associated with a specific state of a biological environment including but not limited to a phase of cellular cycle, health, and disease state. The presence, absence, reduction, upregulation of the biomarker is associated with and is indicative of a particular state. The term "biological environment" refers to any biological setting, including, for example, ecosystems, orders, families, genera, species, subspecies, organisms, tissues, cells, viruses, organelles, cellular substructures, prions, and samples of biological origin. Exemplary chemical analytes include molecular targets such as small molecules, proteins, nucleic acids, and also cells, tissues, and organisms.

The term "spectroscopic probe" indicates a substance that is suitable to be detected based on an interaction between a radiation and the substance through a spectroscopic instrument. Exemplary spectroscopic probes comprise Raman probes and fluorescence probes. The terms "Raman active molecule" or "Raman probe" as used herein refer to a molecule capable having a polarization-dependent vibrational mode excited by an incident light. The vibrational energy stored in the molecule is transformed into a scattering light corresponding to a specific frequency. In particular, detected signals emitted by Raman probes can take the form of Raman spectra. Accordingly, in Raman spectra for a certain Raman probe, each peak represents the vibrational frequency corresponding to resonance energy of the functional groups in the Raman probe as detected. Therefore, Raman spectra are intrinsic properties of the molecules such as a "molecular fingerprint" to identify the molecule without need to use of any additional labels.

In some embodiments, Raman probes suitable to be included in the chemical analyte include Raman-active molecules having polarization-dependent rotational modes. Exemplary Raman probes suitable to be used in the chemical analyte include trans-1,2 bis-(4-pyridyl) ethylene (BPE), Cy-3, Cy-3.5, Cy-5, Cy-5.5, Cy-7, Rhodamine 6G (R6G), methylene blue (MB), 5-carboxyfluorescein or 6-carboxyfluorescein (FAM), N,N,N',N'-tetramethyl-6-carboxyrhodamine (TAMRA), 6-carboxy-4,7,2',7'-tetrachlorofluorescein (TET), 6-carboxy-Xrhodamine (ROX), (3-(5,6,4',7'-tetrachloro-5'-methyl-3',6'-dipivaloylfluorescein-2-yl)-propanamidohexyl-1-O-(2-cyanoethyl)-(N,N-diisopropyl)) Yakima Yellow®, 6-(((4(4,4-difluoro-5-(2-thienyl)-4-bora-3a,4a-diaza-s-indacene-3-yl)phenoxy)acetyl)amino) hexanoic acid (BODIPY TR-X) and additional probes identifiable by a skilled person upon reading of the present disclosure.

The term "fluorescent probe" indicates a substance that is detectable through emission of a visible light by the substance following absorption by the same substance of light of a differing, usually nonvisible, wavelength. Exemplary fluorescent probes suitable in the chemical analyte include Cy-3, Cy-3.5, Cy-5, Cy-5.5, Cy-7, Rhodamine 6G (R6G), methylene blue (MB), TAMRA, and additional probes identifiable by a skilled person.

The term "attach" or "attached" refers to connecting or uniting by a bond or other link or force that keeps two or more components together, which encompasses either direct or indirect attachment where, for example, a first molecule is directly bound to a second molecule or material, or one or more intermediate molecules are disposed between the first molecule and the second molecule or material. The term "bind", "binding", and "conjugation" indicates an attractive interaction between two elements that results in a stable association of the elements in which the elements are in close proximity to each other. Attractive interactions include both non-covalent binding and covalent binding. Non-covalent binding indicates a type of chemical bond, such as protein-protein interaction, that does not involve the sharing of pairs of electrons, but rather involves more dispersed variations of electromagnetic interactions. Non-covalent bonding includes ionic bonds, hydrophobic interactions, electrostatic interactions, hydrogen bonds, and dipole-dipole bonds. Electrostatic interactions include association between two oppositely charged entities.

According to an exemplary embodiment, spectroscopic probes, such as methylene blue, can be attached to the chemical analyte formed by an oligonucleotide through active ester coupling to an amine group (e.g. a 3' C7 amine of an oligonucleotide aptamer).

In some embodiments, a spectroscopic probe, and in particular a Raman probe, can be attached to the chemical analyte by a covalent bond, with or without one or more intermediate molecules, to any position where attachment does not interfere with binding to the aptamer or hybridization to the chemical analyte.

The wording "specific" or "specificity" with reference to hybridization or binding of the chemical analyte or generally of a first molecule to a second molecule refers to the recognition, contact, and formation of a stable complex between the first molecule and the second molecule, together with substantially less to no recognition, contact and formation of a stable complex between each of the first molecule and the second molecule with other molecules that may be present. Exemplary specific bindings include polynucleotide hybridization. The term "specific" as used herein with reference to a sequence of a polynucleotide refers to the unique association of the sequence with a single polynucleotide which is the complementary sequence.

In some embodiment, a nucleic acid core of a DNA switch is immobilized through electrostatic forces to a suitable substrate so that the spectroscopic probe attached to chemical analyte is likewise immobilized to the nucleic acid core proximate to the substrate.

In several embodiments, DNA switch 209 or biomarker signal amplifier 208 herein described can detect chemical analytes with a high sensitivity showing a limit of detection≤100 pM and more particularly within a dynamic range spanning from about 100 pM to about 1 pM depending on the assay performed.

In several embodiments, DNA switch 209 or biomarker signal amplifier 208 can detect chemical analytes with high specificity, wherein the selective hybridization of the chemical analyte to DNA switch 209 or biomarker signal amplifier 208 over other analytes can be shown by specific discrimination of the chemical analyte via electrical detection or optical detection.

DNA nanotechnology-based biomarker measurement platform 200 includes biomarker signal amplifier 208, DNA switch 209, or sensor array 217 configured to perform quantitative biomolecule sensing or to amplify chemical analyte binding. In an embodiment, with reference to FIG.

1, biomarker signal amplifier 208 for amplifying chemical analyte binding includes: analysis substrate 205; surface strand 204 disposed on analysis substrate 205 and including exchange region 207; particle strand 206 hybridized to surface strand 204 in an absence of chemical analyte 203 that preferentially hybridizes to exchange region 207 as compared with particle strand 206, and particle strand 206 is dissociated from surface strand 204 when surface strand 204 is in a presence of chemical analyte 203; and reporter particle 201 attached to particle strand 206 and disposed proximate to analysis substrate 205 when particle strand 206 is hybridized to surface strand 204 in absence of chemical analyte 203 and that changes the electrical potential of analysis substrate 205 depending on whether particle strand 206 is hybridized to surface strand 204.

In an embodiment, with reference to FIG. 2, FIG. 6, FIG. 7, FIG. 8, FIG. 9, FIG. 10, FIG. 11, and FIG. 12, DNA switch 209 for amplifying chemical analyte binding incudes: analysis substrate 205; DNA nanostructure framework 202 disposed on analysis substrate 205 including nucleic acid core 210, first helix strand 211 protruding from nucleic acid core 210 and attached to analysis substrate 205, and second helix strand 212 protruding from nucleic acid core 210 such that second helix strand 212 is hybridized to first helix strand 211 in an absence of chemical analyte 203 that preferentially hybridizes to first helix strand 211 as compared with second helix strand 212, and second helix strand 212 dissociates from first helix strand 211 when first helix strand 211 is in a presence of chemical analyte 203; particle strand 206 hybridized to second helix strand 212; and reporter particle 201 attached to particle strand 206 and disposed proximate to analysis substrate 205 when second helix strand 212 is hybridized to first helix strand 211 in absence of chemical analyte 203 and that changes the electrical potential of analysis substrate 205 depending on whether second helix strand 212 is hybridized to first helix strand 211.

In an embodiment, reporter particle 201 includes a nanoparticle, a quantum dot, a charged polymer, or a combination thereof. The nanoparticle of reporter particle 201 can include a gold nanoparticle. The nanoparticle of reporter particle 201 can have a surface charge.

In an embodiment, reporter particle 201 includes a spectroscopic probe such as a fluorophore, Raman probe, or the like disposed on a nanoparticle.

In an embodiment, chemical analyte 203 includes a nucleic acid, DNA, RNA, or a combination thereof. According to an embodiment, with reference to FIG. 8, chemical analyte 203 includes aptamer 215 and analyte 216. The analyte can include a spectroscopic probe, chemical functional group, and the like.

In an embodiment, surface strand 204 includes single stranded DNA.

In an embodiment, particle strand 206 includes a base sequence that is complementary to the single stranded DNA of the surface strand 204.

In an embodiment, analysis substrate 205 includes a metal, a glass, a ceramic, or a combination thereof on which the other components of biomarker signal amplifier 208 or DNA switch 209 can be disposed.

In an embodiment, DNA switch 209 further includes signal readout in electrical communication with analysis substrate 205 and that receives electrical signal from analysis substrate 205 that changes in response to binding of chemical analyte 203 to surface strand 204.

In an embodiment of DNA switch 209, when chemical analyte 203 is hybridized to first helix strand 211, reporter particle 201 remains attached to nucleic acid core 210 and is sterically or thermodynamically precluded from interacting with first helix strand 211.

In an embodiment, DNA nanostructure framework 202 includes a 2D nanostructure. Exemplary 2D nanostructures include wireframes of polynucleotides, DNA origami, and the like such as 2D arrays.

In an embodiment, DNA nanostructure framework 202 includes a 3D nanostructure. Exemplary 2D nanostructures include wireframes of polynucleotides, DNA origami, and the like such as polyhedral, bundles, and the like. According to an embodiment, DNA nanostructure framework 202 is a DNA backbone helix.

In an embodiment, DNA switch 209 includes signal readout in electrical communication with analysis substrate 205 that receives electrical signal from analysis substrate 205 and that changes in response to binding of chemical analyte 203 to first helix strand 211.

Figure 6:
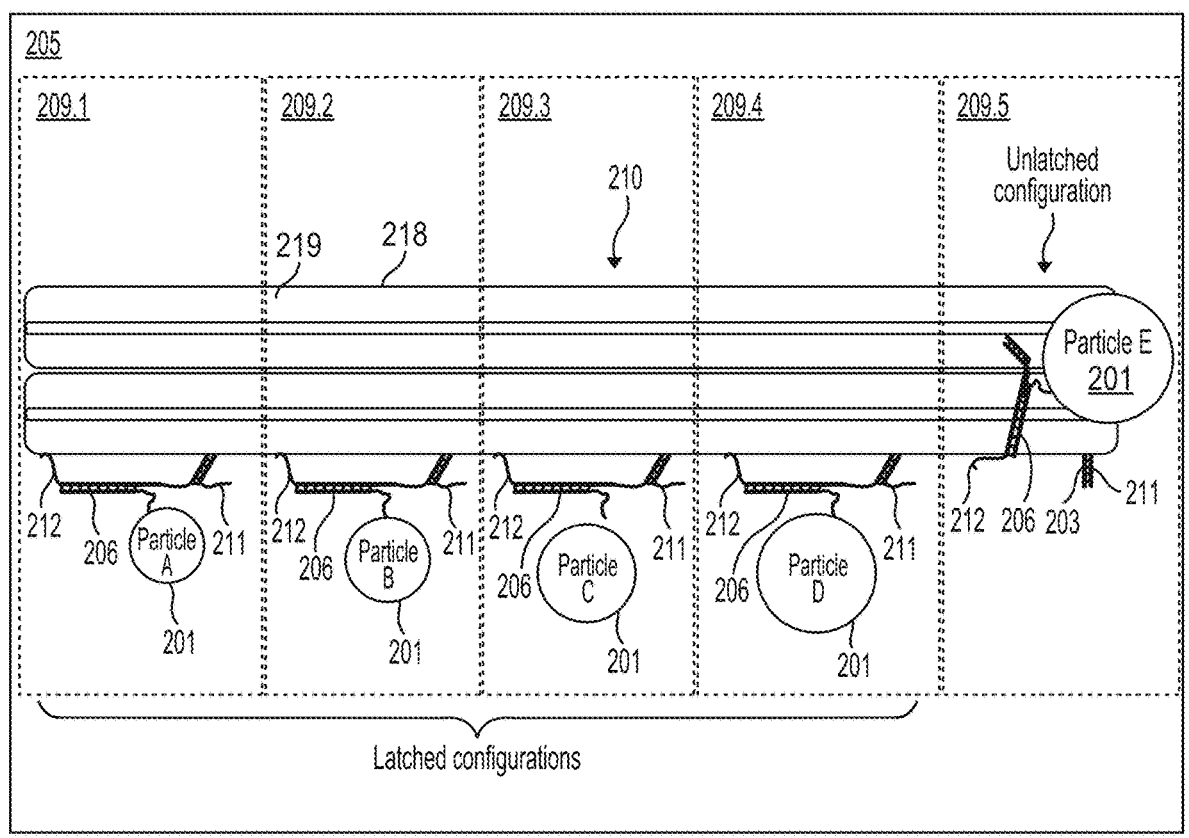
FIG. 6 shows a plurality of DNA switch configured to independently latch and an unlatch in response to selectively hybridizing to separate chemical analytes, wherein sequence specific binding site definition provides precise control of the placement of the analyte interaction sites, and each site is customized to detect different species of chemical analytes for multi-chemical analyte measurements. Diverse reporter particle properties at each analyte binding site provide variable gain amplifiers that return a unique signal for each bound chemical analyte.
Figure 7:
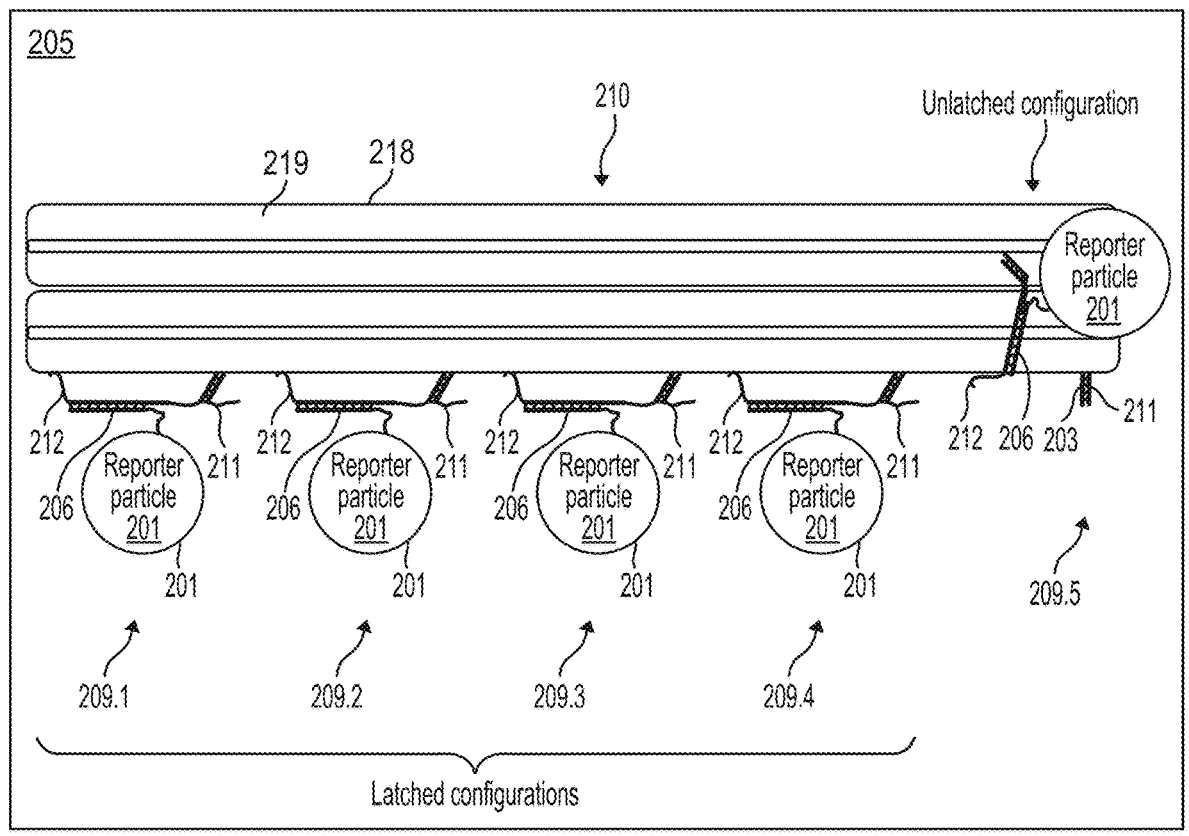
FIG. 7 shows a plurality of DNA switch configured to independently latch and an unlatch in response to selectively hybridizing to separate chemical analytes, wherein the DNA switches have different sensitivity to the chemical analytes, wherein quantitative analyte concentrations measurements are performed with multi-site DNA-based sensing.

In an embodiment of DNA switch 209, with reference to FIG. 6, FIG. 7, FIG. 9, and FIG. 10, a plurality of first helix strands 211 and second helix strands 212 protrude from nucleic acid core 210 with each second helix strand 212 hybridized to a separate first helix strand 211 in absence of chemical analyte 203; and each second helix strand 212 is hybridized to a separate particle strand 206 such that each particle strand 206 is independently attached to a separate reporter particle 201. In an embodiment, at least one of the first helix strands 211 has a different nucleic acid base sequence so that DNA nanostructure framework 202 simultaneously detects multiple different chemical analyte 203. In an embodiment, DNA nanostructure framework 202 is configured to barcode chemical signatures from multiple different chemical analyte 203 as shown in FIG. 6. In an embodiment of DNA switch 209, DNA nanostructure framework 202 is configured to measure the concentration of chemical analyte 203 as shown in FIG. 7.

Figure 10:
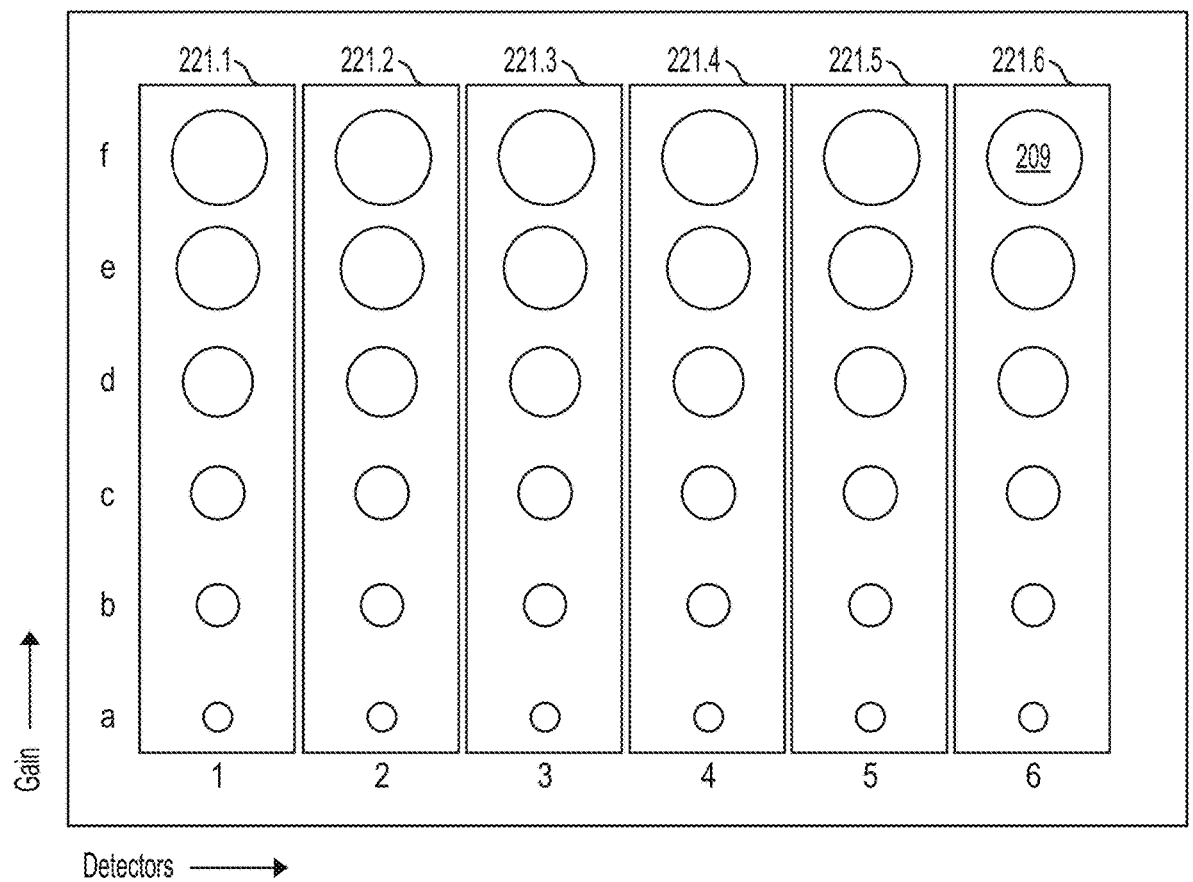
FIG. 10 shows a sensor array that includes six detector elements (gold) to each read six sensor sites (red). Each sensor site is identified by the size of the reporter particle at that location (i.e., gain of the sensor) to allow measurements with spatial resolution across the 2D grid of sensors.
Figure 11:
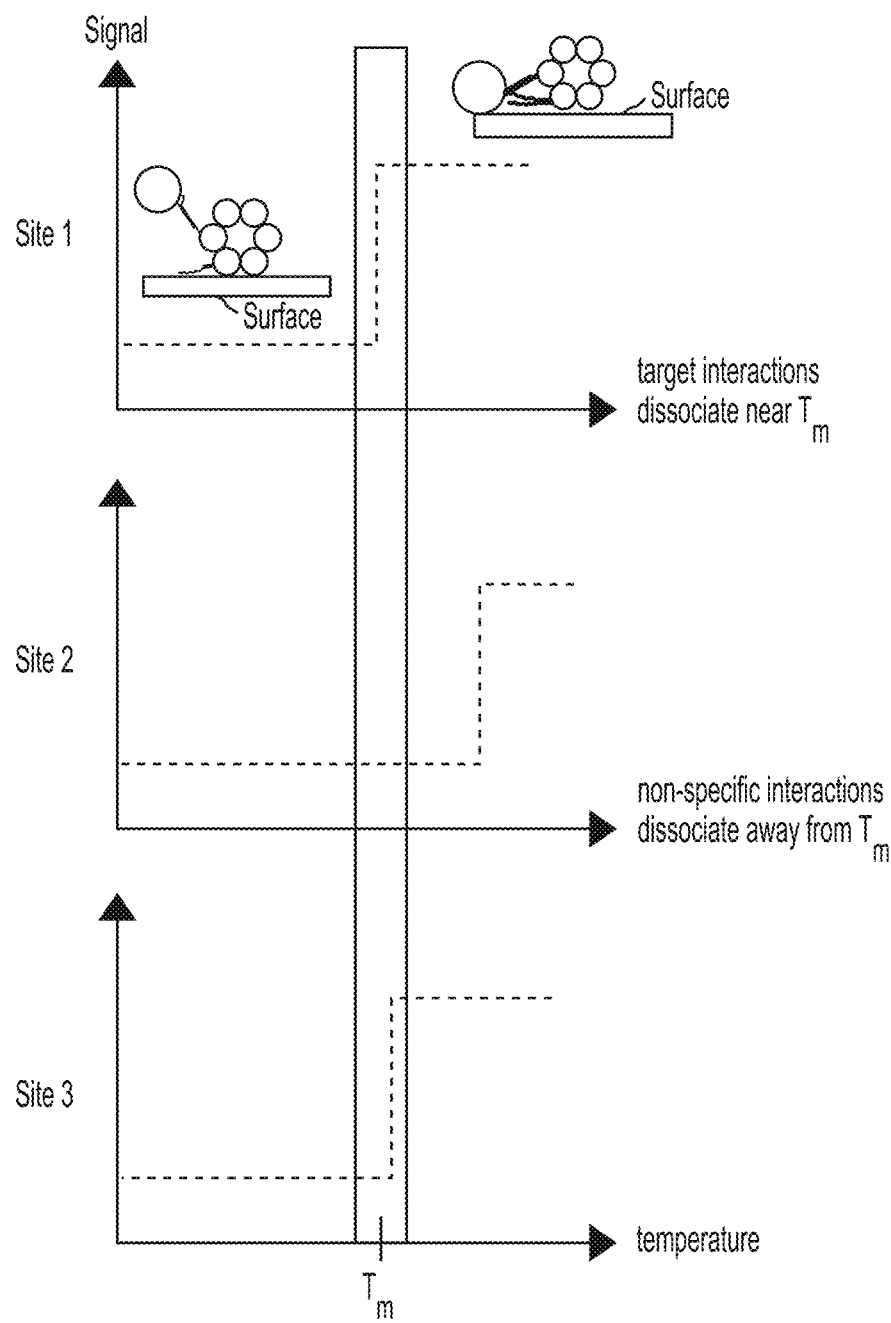
FIG. 11 shows tuning melt temperature Tm of target interactions for separation of specific target interactions from non-specific interactions.

In an embodiment, with reference to FIG. 10, sensor array 217 performs spatially resolved biomarker measurements, wherein sensor array 217 includes a plurality of DNA switches 209 arranged in an array, wherein the plurality of first helix strands 211 independently hybridize separate chemical analytes 203 and produce individual electrical signals that are indicative of presence and absence of chemical analyte 203 at individual first helix strands 211.

Elements of DNA nanotechnology-based biomarker measurement platform 200 and its components can be various sizes and can be varied by a choice of materials.

It is contemplated that large nanoparticles (e.g., with large surface charge or decorated with fluorophores and the like) integrated within a DNA nanostructure framework amplify electrical signal generated in presence of a chemical analyte. With reference to FIG. 1, a single-stranded DNA as surface strand 204 is attached to a surface of analysis substrate 205 (e.g., gold, silica, and the like etc.) using a chemical attachment (e.g., thiol chemistry, silane chemistry, and the like). Reporter particle 201 (e.g., gold nanoparticle, quantum dot, large charged polymer, and the like) with a complementary DNA strand as particle strand 206 is hybridized with surface strand 204 to attach reporter particle 201 in proximate to the surface of analysis substrate 205. The ability to use DNA nanostructures to confine reporter particle 201 proximate to the surface provides a sensitive detection modality such as electronic detection via an electronic signal.

Surface strand 204 can include exchange region 207, capable of interacting with chemical analyte 203 (e.g., DNA, RNA, or other analytes 216 when using a molecular adapter such as aptamer 215) of interest with a higher affinity than particle strand 206. Upon addition of chemical analyte 203, particle strand 206 and thereby reporter particle 201 is displaced from analysis substrate 205 and can be released into solution, resulting in a loss of signal. Therefore, addition of a relatively small-sized chemical analyte 203 results in displacement of a much larger reporter particle 201, which in turn amplifies the effect of binding of chemical analyte 203 to exchange region 207 in biomarker signal amplifier 208.

Figure 2:
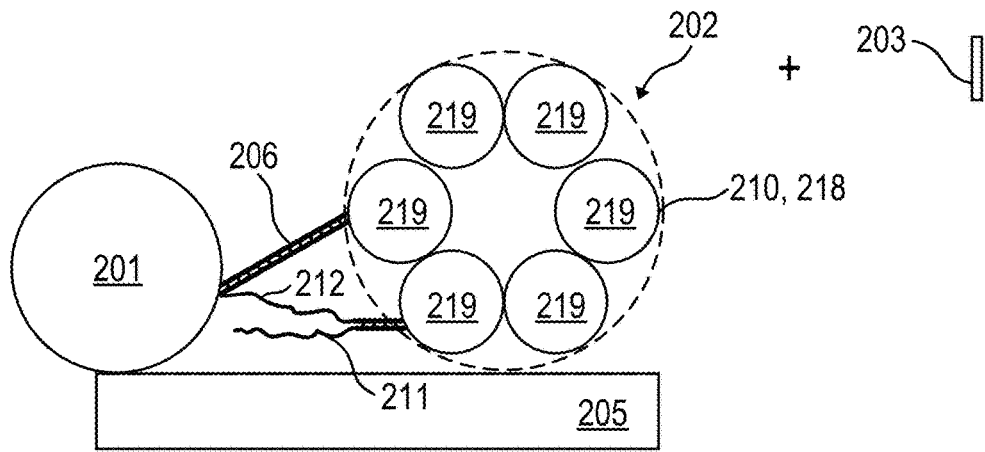
FIG. 2 shows a DNA switch before binding a chemical analyte in panel A and after binding the chemical analyte in panel B, wherein the DNA switch is configured for robust signal amplification upon analyte binding.
Figure 2:
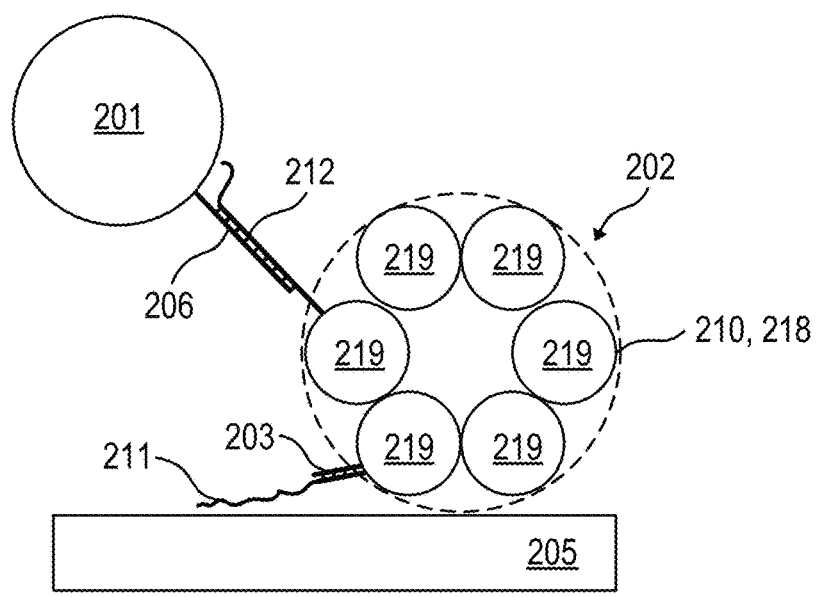
Figure 3:
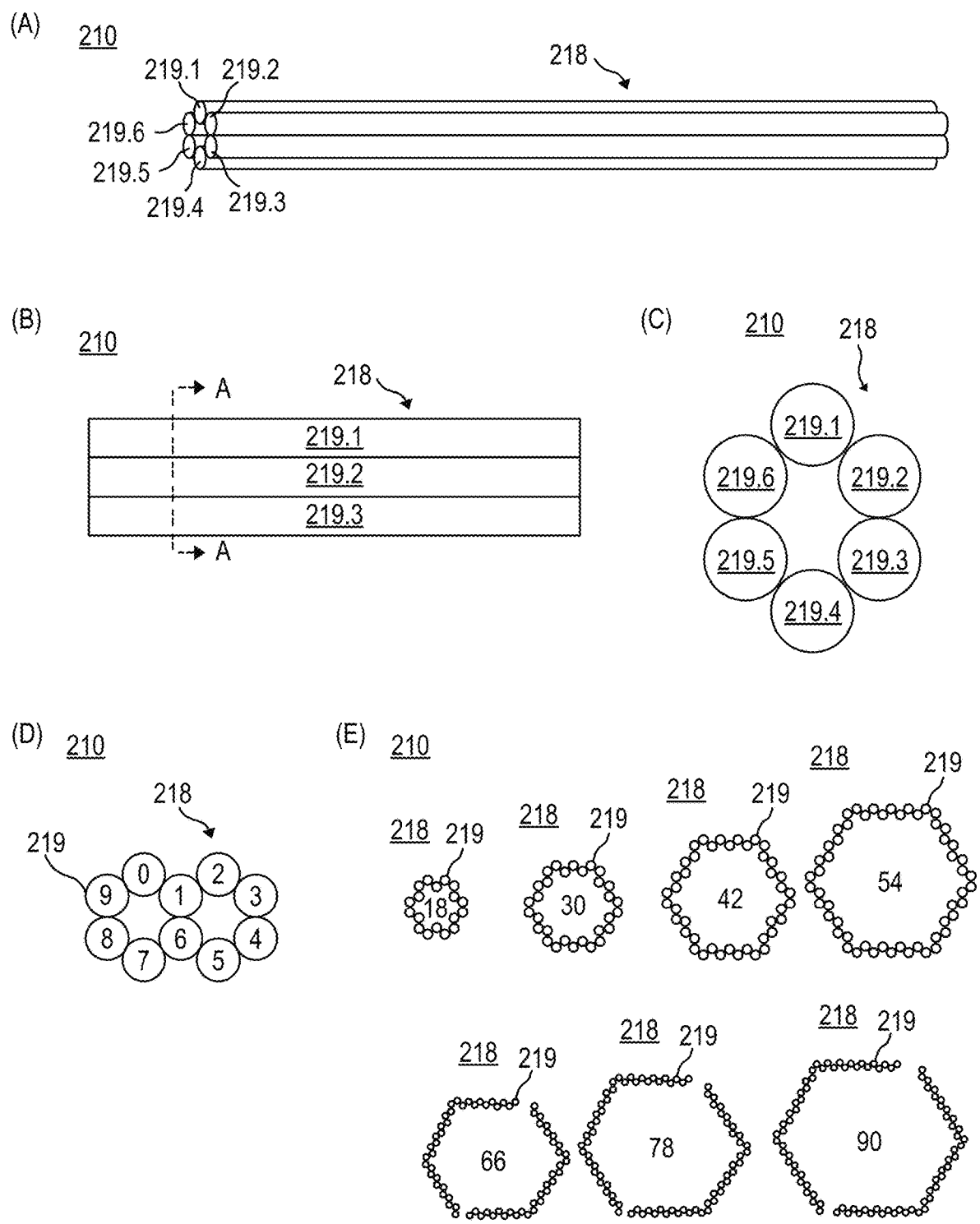
FIG. 3 shows: (panel A) a perspective view of a nucleic acid core that includes a DNA helix bundle for six DNA helixes; (panel B) a side view of the nucleic acid core shown in panel A; (panel C) a cross-section along line A-A of the nucleic acid core shown in panel B; (panel D) a cross-section of a DNA helix bundle that includes ten DNA helixes arranged in a lemniscate configuration; and (panel E) cross-sections of various DNA helix bundles that includes different numbers of DNA helixes indicated by the number located centrally for each DNA helix bundle.
Figure 4:
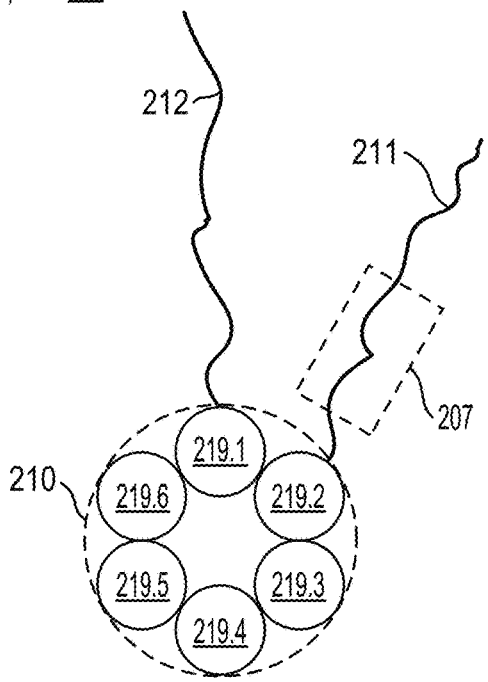
FIG. 4 shows: (panel A) an end view of a DNA nanostructure framework with a second helix strand unhybridized from a first helix strand but hybridized with a particle strand on which is disposed a reporter particle in an unlatched configuration; (panel B) a side view of the DNA nanostructure framework shown in panel A; (panel C) an end view of a DNA nanostructure framework with a second helix strand hybridized to a first helix strand; and (panel D) a side view of the DNA nanostructure framework shown in panel C.
Figure 4:
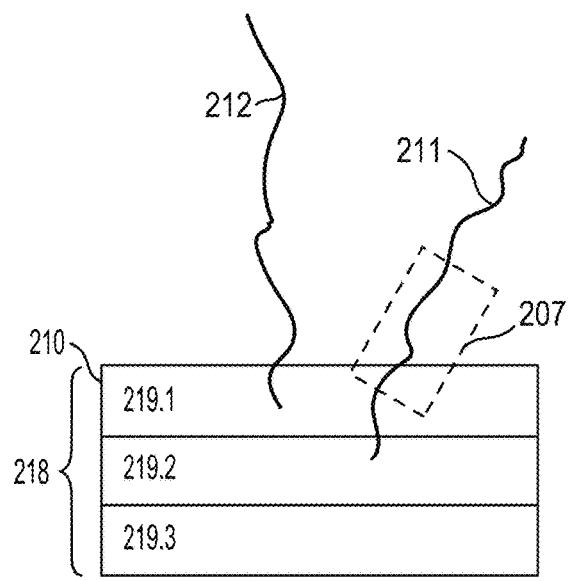
Figure 4:
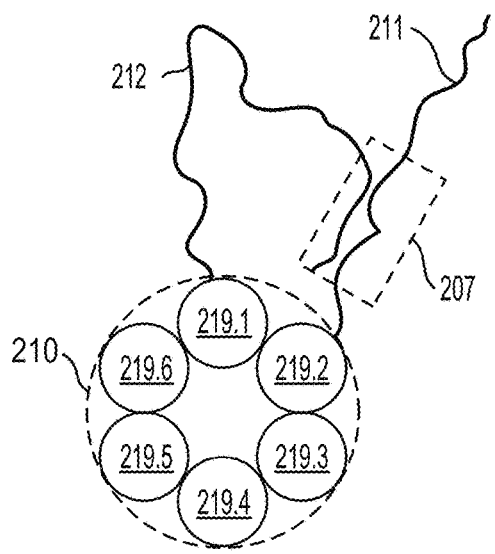
Figure 4:
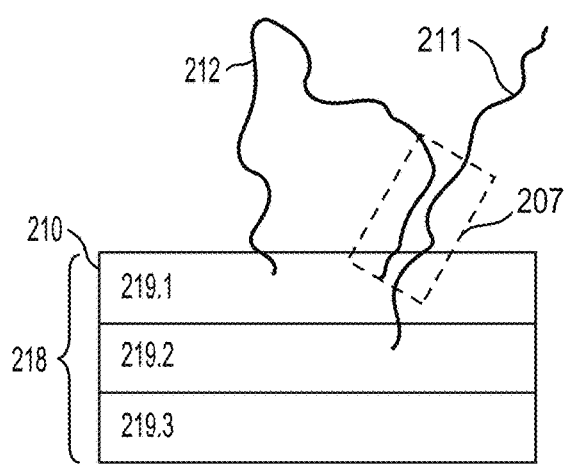
Figure 5:
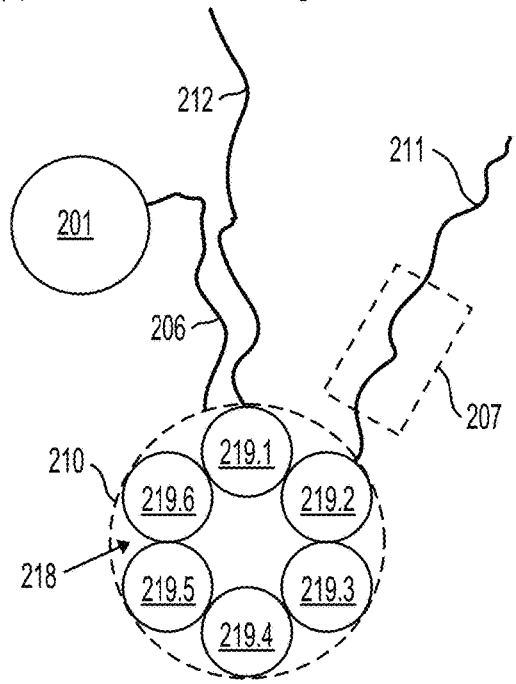
FIG. 5 shows: (panel A) an end view of a DNA nanostructure framework with a second helix strand unhybridized from a first helix strand; (panel B) a side view of the DNA nanostructure framework shown in panel A; (panel C) an end view of a DNA nanostructure framework with a second helix strand hybridized to a first helix strand and a particle strand on which is disposed a reporter particle in an latched configuration; and (panel D) a side view of the DNA nanostructure framework shown in panel C.
Figure 5:
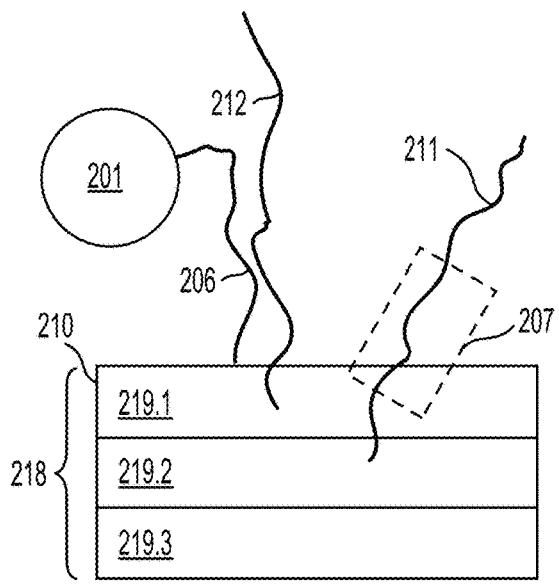
Figure 5:
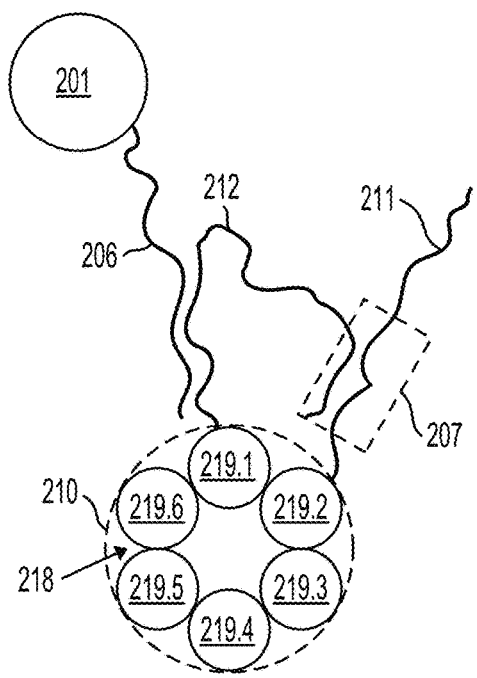
Figure 5:
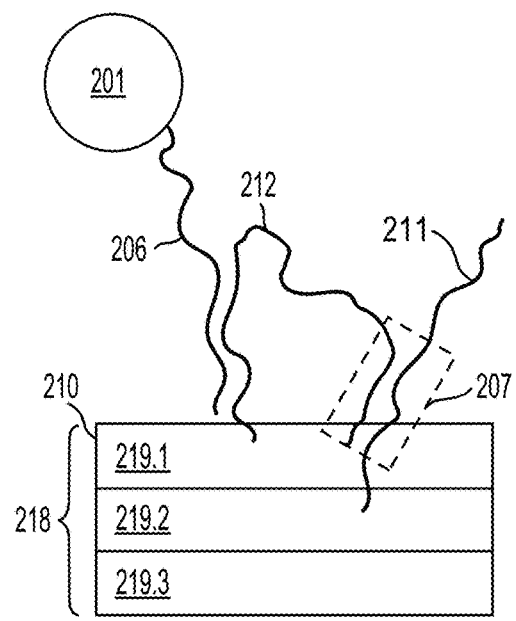

Regarding DNA switch 209, for robust signal amplification, DNA switch 209 provides selective rather than non-specific binding of chemical analyte 203 (e.g., from unintended interactions between released reporter particle 201 and analysis substrate 205) that could otherwise result in erroneous kinetics measurement. DNA switch 209 minimizes non-specific interactions with chemical analyte 203. While the configuration shown in FIG. 2 includes DNA helix bundle 218 as nucleic acid core 210, nucleic acid core 210 is not limited to just DNA helix bundle 218. Indeed, a variety of 2D and 3D DNA nanostructures for nucleic acid core 210 supports functions of DNA switch 209 described here. With reference to FIG. 2, FIG. 3, and FIG. 4, nucleic acid core 210 can includes DNA helix bundle 210 that includes DNA helixes 219, e.g., six DNA helixes 219 (including first DNA helix 219.1, second DNA helix 219.2, third DNA helix 219.3, fourth DNA helix 219.4, fifth DNA helix 219.5, sixth DNA helix 219.6), ten DNA helixes, and the like.

In the configuration shown in FIG. 2, nucleic acid core 210 is assembled with reporter particle 201 including particle strand 206 that can be a DNA strand hybridized with both second helix strand 212 and first helix strand 211. This configuration can restrict reporter particle 201 to be proximate to the surface of analysis substrate 205 where reporter particle 201 can be detected using a sensing approaches discussed below. Upon addition of chemical analyte 203, which preferentially binds first helix strand 211 with the strand displacement shown in panel B of FIG. 1, reporter particle 201 is displaced from being proximate to analysis substrate 205 and moves distally away from analysis substrate 205 as shown in panel B of FIG. 2, indicating bound chemical analyte 203. Advantageously, when chemical analyte 203 is bound by DNA switch 209 through hybridization not first helix strand 211, reporter particle 201 is still constrained to DNA helix bundle 218 of nucleic acid core 210. Furthermore, reporter particle 201 is sterically and thermodynamically precluded from interacting with first helix strand 211, minimizing any non-specific interactions with analysis substrate 205.

In an embodiment, DNA switch 209 has tunable sensitivity toward chemical analyte 203. As unlatching of reporter particle 201 from analysis substrate 205 is mediated by binding competition between second helix strand 212 and chemical analyte 203 binding for first helix strand 211 sequence, the sensitivity of the displacement of reporter particle 201 with respect to analysis substrate 205 can be tuned by changing the predetermined second helix strand 212/first helix strand 211 affinity via sequence length. This tuning can simultaneously modify the thermodynamics (ultimate binding affinity) and kinetics (binding rate) with respect to chemical analyte 203. As thermodynamics and kinetics can be measured from the same signal readout, and they can be characterized for chemical analyte 203 to provide an internal consistency check for detection of chemical analyte 203.

With regard to the signal readout, biomarker signal amplifier 208 and DNA switch 209 are compatible with multiple readout methods that include but are not limited to the following techniques. When reporter particle 201 with a large surface charge is used (e.g., Au nanoparticles with a high surface coverage of DNA, and the like) with analysis substrate 205 that is connected to a charge sensitive electronic readout system (e.g., field-effect transistors, amplifiers, and the like), a large change in the surface potential at the input of the electronics interface results that is easily detected. Exemplary readout systems are described in U.S. patent application Ser. Nos. 16/220,866, 16/867,590, and 17/029,999, the disclosures of which are incorporated herein by reference in their entirety.

For reporter particle 201 that is either large so reporter particle 201 can be resolved optically or have fluorescent properties (e.g., nanoparticles covered with a fluorophore, quantum dots, and the like), measurements can be performed optically. A direct approach is to detect a loss of fluorescence upon binding chemical analyte 203 to first helix strand 211. In an embodiment, reporter particles 201 can include a quenching molecule that suppresses emission of fluorophores attached to analysis substrate 205. Upon binding chemical analyte 203, the quenching molecules are removed because reporter particle 201 is displaced away from analysis substrate 205, resulting in a fluorescence signal.

In an embodiment, surface probe imaging techniques such as atomic force microscopy (AFM) directly image the presence or absence of the reporter particles 201 to determine binding of chemical analyte 203 to first helix strand 211.

Signals output by each readout approach can be processed to extract information about the type or concentration of chemical analyte 203. Because biomarker signal amplifier 208 and DNA switch 209 leverages nanoscale features of DNA constructs, such can be formatted into a sensor array to simultaneously measure a spatial distribution of chemical analytes 203 that can be suited for processing with the pattern recognition capabilities of artificial intelligence (AI) or machine learning (ML) algorithms. Such approaches include but are not limited to deep neural networks (DNNs), neuromorphic elements, or other software or hardware components.

Figure 9:
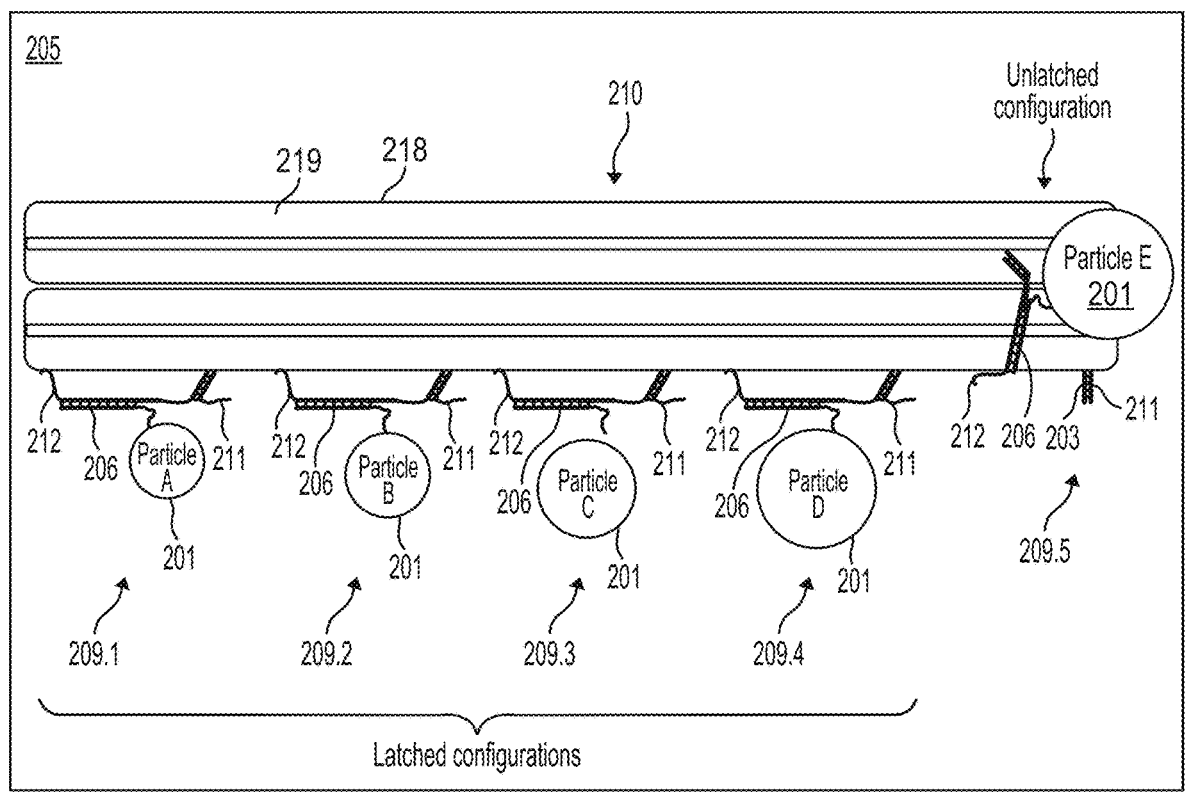
FIG. 9 shows diverse reporter particle properties at each analyte binding site that provide variable gain amplifiers that produce a unique electrical signal for each bound analyte as shown in the graph of electrical signal produced by the DNA switches.
Figure 9:
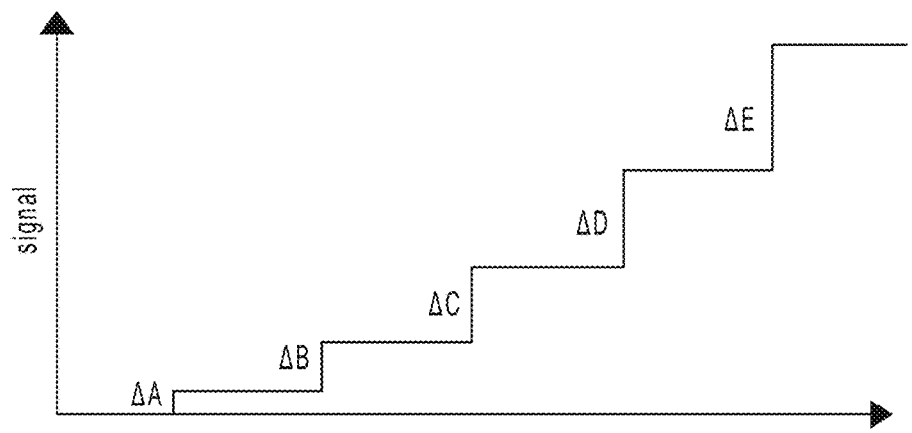

With regard to multiple sensing sites for chemical analytes 203 such as shown in FIG. 6, FIG. 7, and FIG. 9, DNA helix bundle 218 of nucleic acid core 210 provides the sequence-specific definition for of multiple sensing sites. For receptor concentration, attaching reporter particles 201 at specific locations along helix bundle 218 precisely defines the number of binding sites and their location. Such a precise definition of receptor sites and their surface concentration is advantageous for array testing. For multi-chemical analyte sensing, each interaction site provided by separate DNA switches (e.g., 209.1, 209.2, . . . , 209.k, wherein k is an integer number of such switches) can be customized to be sensitive to a specific chemical analyte 203 of interest. This allows a single helix bundle 218 to simultaneously detect multiple chemical analytes 203. Additional sensing configurations can optimize measurement to enhance statistical sampling, account for readout resolution, and the like.

In an embodiment, a plurality of DNA switches 209 is configured for barcoding logic. As shown in FIG. 9, DNA nanotechnology-based biomarker measurement platform 200 determines barcode chemical signatures from multiple chemical analytes 203 in a solution. In an aspect, DNA nanotechnology-based biomarker measurement platform 200 is applied to detecting specific DNA/RNA sequences of chemical analyte 203, wherein first DNA switch 209.1 (referred to as site A) is sensitive to sequence 1, site B 209.2 to sequence 2, etc. A positive test result may be determined when site A 209.1 and site C 209.3 are activated, but not site D. The Boolean logic for such a measurement is accordingly (A && C && !D). Thus, the flexibility of sequence-specific detection sites 209.$k$ simplifies detection of complex chemical signatures from a mixture of chemical analytes 203 that have different nucleic acid sequences.

In an embodiment, with reference to FIG. 7, DNA nanotechnology-based biomarker measurement platform 200 provides analyte concentration measurements. Here, tunable energetics along DNA helix bundle 218 provide chemical analyte interaction sites 209.$k$ to more sensitive or less sensitive to presence of chemical analyte 203 and construction of a ladder or scale, allowing determination of concentration of chemical analyte 203 from the binding position along DNA helix bundle 218 corresponding to DNA switch 209.$k$.

As reporter particle 201 and chemical analyte 203 strands undergo competition via strand displacement to first helix strand 211, energetics of binding can be tuned using the size of toehold regions (see FIG. 12) for particle strand 206 and chemical analyte 203 strands, and the shared competition regions between the two. DNA nanotechnology-based biomarker measurement platform 200 in FIG. 7 can be tuned so that each DNA switch 209 senses the same type of chemical analyte 203 but with a different sensitivity toward chemical analyte 203. This in turn will allow higher concentrations of chemical analyte 203 to interact more strongly with certain sites 209.$k$ along DNA helix bundle 218 than would otherwise occur, providing accurate quantification of concentration of chemical analyte 203. Precisely defining the affinity of each sensing site 209.$k$ for a particular chemical analyte 203 allows measurements across a broad dynamic range than with conventional sensing methods. Furthermore, the defined dynamic range is tunable to fit the target application.

As strand displacement-based tuning described above simultaneously modifies both the equilibrium energetics and the kinetic rates of the reaction, the combination of the rate of signal change with the amplifier gain of biomarker signal amplifier 208 or DNA switch 209 provides a simultaneous measure of concentration of chemical analyte 203 that can be a metric for quality control.

Figure 8:
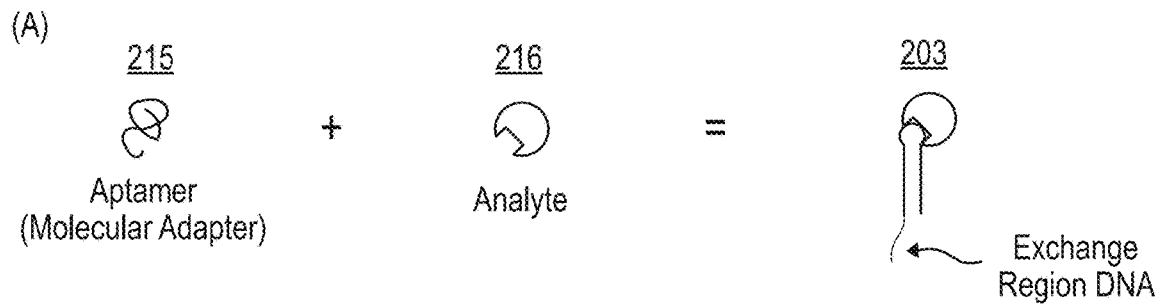
FIG. 8 shows: (panel A) formation of a chemical analyte from an aptamer and an analyte; (panel B) a DNA switch in a latched configuration wherein a second helix strand is hybridized to a first helix strand; and (panel C) the DNA switch in an unlatched configuration wherein the second helix strand is unhybridized to the first helix strand that is hybridized to the chemical analyte, wherein molecular adapters (e.g., aptamers) conjugate to probe DNA molecules that provide a variety of recognition elements.
Figure 8:
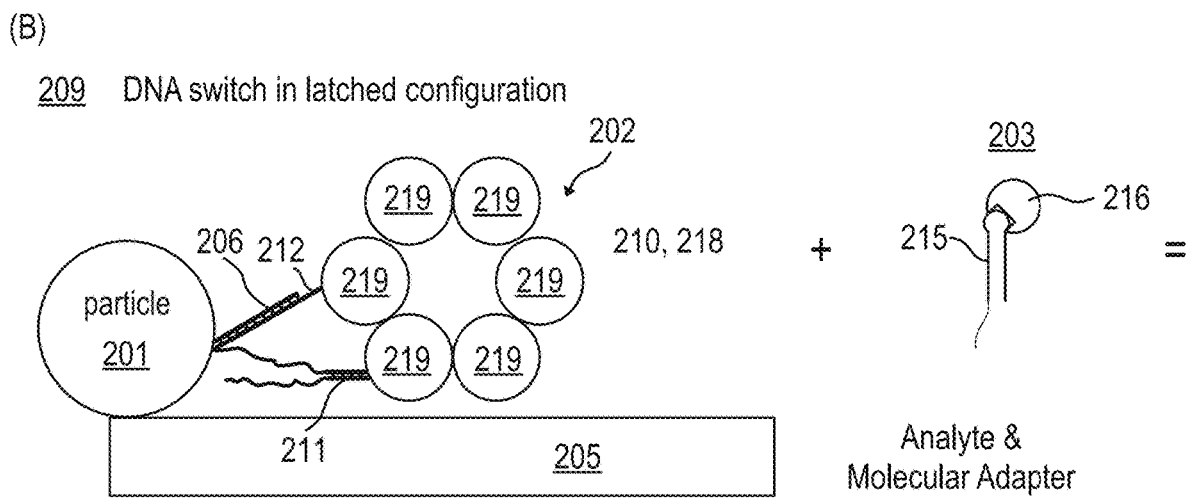
Figure 8:
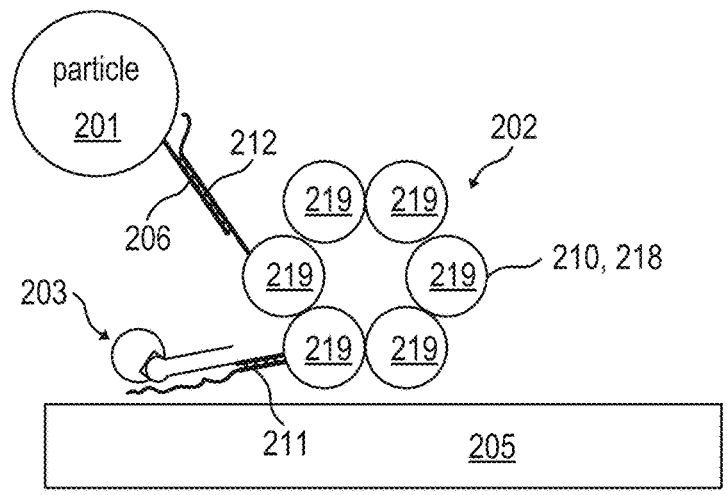

In an embodiment, chemical analyte 203, biomarker signal amplifier 208, or DNA switch 209 can include a molecular adapter, e.g., chemical analyte 203 as shown in FIG. 8. Molecular adapters can be, e.g., an aptamer, antibody, protein, and the like that can be conjugated to probe DNA strands for recognition of various target analytes, e.g., analyte 216, in solution to form chemical analyte 203. FIG. 8 shows aptamer 215 that captures target analyte 216 in solution and forms chemical analyte 203. When analyte 216 is bound to aptamer 215, aptamer 215 changes conformation to provide aptamer exchange region to be activated. The DNA probe strands (e.g., aptamer exchange region) attached to aptamer 215 in chemical analyte 203 interact with sites (e.g., first helix strand 211) on DNA helix bundle 218 of nucleic acid core 210 to displace reporter particle 201. This modular approach provides DNA nanotechnology-based biomarker measurement platform 200 to rapidly adapt to particular applications. DNA nanotechnology-based biomarker measurement platform 200 with aptamer 215-based chemical analyte 203 also allows commonly used approaches such as sandwich antibody assays to be adapted for use with advances in biotechnology.

Regarding DNA amplifier gain, resolution, and dynamic range, the gain of biomarker signal amplifier 208 or DNA switch 209 can be precisely defined by engineering the properties of reporter particle 201 (e.g., using geometry, surface charge, fluorophore density, and the like). FIG. 9 shows DNA nanotechnology-based biomarker measurement platform 200 that operates as a multi-chemical analyte sensor with a variable gain at each interaction site 209.$k$, defined by the size and charge of individual reporter particles 201. Each analyte binding site of DNA switch 209.$k$ is designed to bind a different type of chemical analyte 203. All binding sites 209 are read with a single electronic detector. When chemical analytes 203 bind to the individual sites 209.$k$ at individual first helix strand 211, the change in the signal (shown in FIG. 9 as $\Delta A$, $\Delta B$, $\Delta C$, and the like) are proportional to the size and charge on the respective reporter particle 201, e.g., particle A, B, C, and the like. When the electronic detector has single particle resolution, the detection of binding events allows determination of the specific site 209 that was activated and therefore the type of chemical analyte 203.

DNA nanotechnology-based biomarker measurement platform 200 provides a one-to-one correspondence between the detection of chemical analyte 203 and its amplification through displacement of reporter particle 201 from analysis substrate 205. The resolution of the measurement is determined by the sensitivity of the detection technique to reporter particle 201. As an example, electrostatic interfacial potential $\zeta$ of a hydrated nanoparticle covered with DNA strands is tens of millivolts so that single molecule discrimination of reporter particles 201 and single molecule detection of bound chemical analyte 203 can be performed. A similar resolution is obtained by using optical and other imaging techniques to measure reporter particles 201 such as fluorescent nanoparticles, quantum dots and the like.

DNA nanotechnology-based biomarker measurement platform 200 provides independent tunability of gain and affinity that allows precise engineering of the relationship between signal, concentration of chemical analyte 203 or analyte 216, and type of chemical analyte 203 or analyte 216. This capability maximizes measurement accuracy over a predetermined concentration range for critical measurement outcomes.

DNA nanotechnology-based biomarker measurement platform 200 can be optimized to tune resolution, to improve specificity to molecules of interest as chemical analyte 203, and to assure quality of the measurement. Sensor configurations of DNA nanotechnology-based biomarker measurement platform 200 can combine the modular components to attain practical measurement implementations.

DNA nanotechnology-based biomarker measurement platform 200 can be configured for engineering gain, affinity, and spatial resolution for quantitative multi-chemical analyte measurements. Engineering the gain and affinity for chemical analyte 203 or a particular type thereof provides optimal tuning of measurement resolution and enables non-conventional sensor designs. With reference to FIG. 6, DNA nanotechnology-based biomarker measurement platform 200 can include a plurality of DNA switches 209 that provide multiple binding sites as first helix strand 211 on nucleic acid core 210 that is sensitive to different chemical species of chemical analyte 203 as discussed above for multi-analyte sensing and barcoding. Further, DNA nanotechnology-based biomarker measurement platform 200 can extract concentration for measurements that extract quantitative analyte concentration.

These configurations and capabilities can be combined or obtained by incorporating nucleic acid core 210 or other DNA nanostructures in an array format such as 2D array of discrete sensors for simultaneous multi-chemical analyte sensing. FIG. 10 shows sensor array 217, wherein each electronic detector 221 includes six DNA-based sensor sites 209 (red). Each sensor site 209 includes a discrete size of reporter particle 201 that determines the gain as described previously. It is contemplated that each detector 221 will have a different affinity for chemical analyte 203, while the gain of individual reporter particles 201 determines the type of chemical analyte 203. Sensor array 217 has a compact configuration for measurements, e.g., of 6 independent chemical analytes 203 and provides determination of a concentration profile, e.g., with 6 data points. By employing six detectors 221, sensing occurs at 36 discrete sites 209, simplifying system design by reducing complexity of readout infrastructure. It should be appreciated that the number of DNA switches 209 per electronic detector 221 and number of electronic detectors 221 are arbitrary and can be selected based on design choice or practical application.

Sensor array 217 shown in FIG. 10 can be a single multi-chemical analyte detector. Small spatial dimensions of sensor array 217 can be, e.g., ≈2 μm per edge, to be a single measurement pixel. This pattern can be then replicated across a 2D grid for multi-chemical analyte sensing over a larger area with high spatial resolution. The technique can enable embedded for chemical measurements within cell and tissue cultures, e.g., in a body-on-a-chip platform, with complex chemical dynamics that are spatially and temporally correlated. Performing multiple multi-chemical analyte measurements also can occur in clinical diagnostics to improve statistics and increase assurance in the quality of a test result.

Optimizations of sensor array 217 to ensure accuracy are contemplated. Regarding specificity and quality assurance, an array of sensing sites 209 provide multiple independent measurements of the same chemical analyte 203, allowing improved statistical sampling and high confidence in results produced. Sensor array 217 can be engineered with a configuration similar to that shown in FIG. 10, wherein each row (indicated with letters "a" to "f") can be sensitive to the same chemical analyte 203. Accordingly, 6 samples of a single chemical analyte with 6 total chemicals are detected.

To improve measurement quality, the pair of chemical analyte 203 and first helix strand 211 have a well-defined melting temperature $T_m$. The melt profile of all interactions in the system can be tuned for the desired binding affinities. Therefore, melting temperature $T_m$ is used to distinguish target interactions from non-specific ones (FIG. 11) and minimizing error rates. Accordingly, DNA switch 209 is heated to a temperature great than melting temperature $T_m$. Target interactions dissociate within a narrow window about melting temperature $T_m$. Non-specific events dissociate outside of this region as shown in the multiple interaction sites in FIG. 11.

Figure 12:
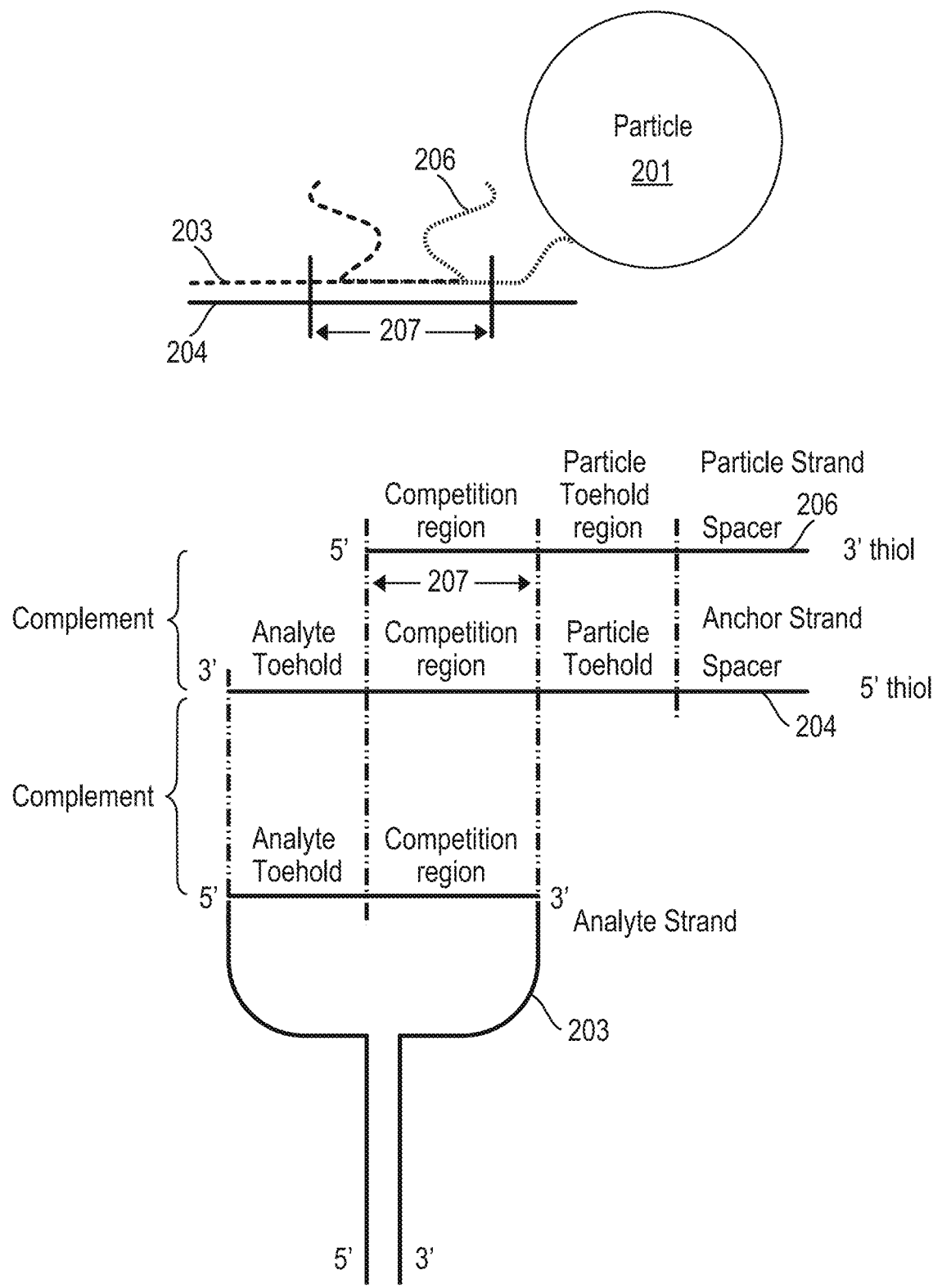
FIG. 12 shows competition regions for detection of MiR-22.

DNA nanotechnology-based biomarker measurement platform 200 Can include biomarker signal amplifier 208 or DNA switch 209 for detecting micro RNA or quantifying radiation induced damage. MicroRNA expression can be used for evaluating situations when a person or item (e.g., in an absence of a dosimeter) has been subjected to an unknown level of ionizing radiation at the population level. Because MicroRNA expression is part of the physiological response to ionizing radiation, testing with DNA nanotechnology-based biomarker measurement platform 200 can quantify exposure post-event and provide data to prioritize medical care for high exposure subjects. While some conventional tests for microRNAs are sensitive, e.g. qPCR assays, some may not be rapid enough to be suited to field conditions nor be suitable for rapid training of testing staff. DNA nanotechnology-based biomarker measurement platform 200 provides a miniaturized, rapid, testing platform for ionizing radiation linked microRNAs, solving these issues of conventional technology. For example, a microRNA identified as MiR-22 has a probable hairpin structures with ssDNA loop over a similar region of the sequence. This loop can be a nucleation point for interaction between MiR-22 and first helix strand 211, as shown above in FIG. 2. Using MiR-22, one tests the absolute change in signal upon reporter particle 201 release and the change in sensitivity that occurs as modification of the size of the chemical analyte toehold and strand competition regions are modified on second helix strand 212 and first helix strand 211. FIG. 12 shows the strand regions for particle strand 206, surface strand 204, and chemical analyte 203.

While one or more embodiments have been shown and described, modifications and substitutions may be made thereto without departing from the spirit and scope of the invention. Accordingly, it is to be understood that the present invention has been described by way of illustrations and not limitation. Embodiments herein can be used independently or can be combined.

All ranges disclosed herein are inclusive of the endpoints, and the endpoints are independently combinable with each other. The ranges are continuous and thus contain every value and subset thereof in the range. Unless otherwise stated or contextually inapplicable, all percentages, when expressing a quantity, are weight percentages. The suffix (s) as used herein is intended to include both the singular and the plural of the term that it modifies, thereby including at least one of that term (e.g., the colorant(s) includes at least one colorants). Option, optional, or optionally means that the subsequently described event or circumstance can or cannot occur, and that the description includes instances where the event occurs and instances where it does not. As used herein, combination is inclusive of blends, mixtures, alloys, reaction products, collection of elements, and the like.

As used herein, a combination thereof refers to a combination comprising at least one of the named constituents, components, compounds, or elements, optionally together with one or more of the same class of constituents, components, compounds, or elements.

All references are incorporated herein by reference.

The use of the terms "a," "an," and "the" and similar referents in the context of describing the invention (especially in the context of the following claims) are to be construed to cover both the singular and the plural, unless otherwise indicated herein or clearly contradicted by context. It can further be noted that the terms first, second, primary, secondary, and the like herein do not denote any order, quantity, or importance, but rather are used to distinguish one element from another. It will also be understood that, although the terms first, second, etc. are, in some instances, used herein to describe various elements, these elements should not be limited by these terms. For example, a first current could be termed a second current, and, similarly, a second current could be termed a first current, without departing from the scope of the various described embodiments. The first current and the second current are both currents, but they are not the same condition unless explicitly stated as such.

The modifier about used in connection with a quantity is inclusive of the stated value and has the meaning dictated by the context (e.g., it includes the degree of error associated with measurement of the particular quantity). The conjunction or is used to link objects of a list or alternatives and is not disjunctive; rather the elements can be used separately or can be combined together under appropriate circumstances.

What is claimed is:

1. A biomarker signal amplifier for amplifying chemical analyte binding, the biomarker signal amplifier comprising:
   an analysis substrate;
   a surface strand disposed on the analysis substrate and comprising an exchange region;
   a particle strand hybridized to the surface strand in an absence of a chemical analyte that preferentially hybridizes to the exchange region as compared with the particle strand, and the particle strand is dissociated from the surface strand when the surface strand is in a presence of the chemical analyte; and
   a reporter particle attached to the particle strand and disposed proximate to the analysis substrate when the particle strand is hybridized to the surface strand in absence of the chemical analyte and that changes the electrical potential of the analysis substrate depending on whether the particle strand is hybridized to the surface strand.

2. The biomarker signal amplifier of claim 1, wherein the reporter particle comprises a nanoparticle, a quantum dot, a charged polymer, or a combination thereof.

3. The biomarker signal amplifier of claim 2, wherein the nanoparticle of the reporter particle comprises a gold nanoparticle.

4. The biomarker signal amplifier of claim 1, wherein the nanoparticle of the reporter particle comprises a surface charge.

5. The biomarker signal amplifier of claim 1, wherein the reporter particle comprises a fluorophore disposed on a nanoparticle.

6. The biomarker signal amplifier of claim 1, wherein the chemical analyte comprises a nucleic acid, DNA, RNA, or a combination thereof.

7. The biomarker signal amplifier of claim 1, wherein the surface strand comprises a single stranded DNA.

8. The biomarker signal amplifier of claim 7, wherein the particle strand comprises a base sequence that is complementary to the single stranded DNA of the surface strand.

9. The biomarker signal amplifier of claim 1, wherein the analysis substrate comprises a metal, a glass, a ceramic, or a combination thereof.

10. The biomarker signal amplifier of claim 1, further comprising a signal readout in electrical communication with the analysis substrate and that receives an electrical signal from the analysis substrate that changes in response to binding of the chemical analyte to the surface strand.

11. A DNA switch for amplifying chemical analyte binding, the DNA switch comprising:
    an analysis substrate;
    a DNA nanostructure framework disposed on the analysis substrate comprising a nucleic acid core, a first helix strand protruding from the nucleic acid core and attached to the analysis substrate, and a second helix strand protruding from the nucleic acid core such that the second helix strand is hybridized to the first helix strand in an absence of a chemical analyte that preferentially hybridizes to the first helix strand as compared with the second helix strand, and the second helix strand dissociates from the first helix strand when the first helix strand is in a presence of the chemical analyte;
    a particle strand hybridized to the second helix strand; and
    a reporter particle attached to the particle strand and disposed proximate to the analysis substrate when the second helix strand is hybridized to the first helix strand in absence of the chemical analyte and that changes the electrical potential of the analysis substrate depending on whether the second helix strand is hybridized to the first helix strand.

12. The DNA switch of claim 11, wherein when the chemical analyte is hybridized to the first helix strand: the reporter particle remains attached to the nucleic acid core, and is sterically or thermodynamically precluded from interacting with the first helix strand.

13. The DNA switch of claim 11, wherein the DNA nanostructure framework comprises a 2D nanostructure.

14. The DNA switch of claim 11, wherein the DNA nanostructure framework comprises a 3D nanostructure.

15. The DNA switch of claim 11, wherein the DNA nanostructure framework comprises a DNA backbone helix.

16. The DNA switch of claim 11, wherein the reporter particle comprises a nanoparticle, a quantum dot, a charged polymer, or a combination thereof.

17. The DNA switch of claim 16, wherein the nanoparticle of the reporter particle comprises a gold nanoparticle.

18. The DNA switch of claim 16, wherein the nanoparticle of the reporter particle comprises a surface charge.

19. The DNA switch of claim 11, wherein the reporter particle comprises a fluorophore disposed on a nanoparticle.

20. The DNA switch of claim 11, wherein the chemical analyte comprises a nucleic acid, DNA, RNA, or a combination thereof.

21. The DNA switch of claim 20, wherein the chemical analyte further comprises an aptamer and an analyte.

22. The DNA switch of claim 11, further comprising a signal readout in electrical communication with the analysis substrate and that receives an electrical signal from the analysis substrate that changes in response to binding of the chemical analyte to the first helix strand.

23. The DNA switch of claim 11, wherein a plurality of first helix strands and second helix strands protrude from the nucleic acid core with each second helix strand hybridized to a separate first helix strand in absence of the chemical analyte; and each second helix strand is hybridized to a separate particle strand such that each particle strand is independently attached to a separate reporter particle.

24. The DNA switch of claim 23, wherein at least one of the first helix strands has a different nucleic acid base sequence so that the DNA nanostructure framework simultaneously detects multiple different chemical analyte.

25. The DNA switch of claim 24, wherein the DNA nanostructure framework is configured to barcode chemical signatures from the multiple different chemical analyte.

26. The DNA switch of claim 23, wherein the DNA nanostructure framework is configured to measure concentration of the chemical analyte.

27. A sensor array for performing spatially resolved biomarker measurements, the sensor array comprising a plurality of the DNA switches of claim 11 arranged in an array, wherein the plurality of first helix strands independently hybridizes separate chemical analytes and produces individual electrical signals indicative of presence and absence of the chemical analyte at individual first helix strands.

* * * * *